United States Patent
Mudde et al.

(10) Patent No.: US 11,154,599 B2
(45) Date of Patent: Oct. 26, 2021

(54) HER2/NEU IMMUNOGENIC COMPOSITION

(71) Applicant: OncoQR ML GmbH, Tullnerbach (AT)

(72) Inventors: Geert Mudde, Breitenfurt (AT); Jorge Sepulveda, Vienna (AT); Christopher Taus, Vienna (AT); Liesbeth Mudde-Boer, Breitenfurt (AT)

(73) Assignee: ONCOQR ML GMBH, Tullnerbach (AT)

( * ) Notice: Subject to any disclaimer, the term of this patent is extended or adjusted under 35 U.S.C. 154(b) by 42 days.

(21) Appl. No.: 15/574,144

(22) PCT Filed: May 17, 2016

(86) PCT No.: PCT/EP2016/061035
§ 371 (c)(1),
(2) Date: Nov. 14, 2017

(87) PCT Pub. No.: WO2016/184862
PCT Pub. Date: Nov. 24, 2016

(65) Prior Publication Data
US 2018/0125953 A1  May 10, 2018

(30) Foreign Application Priority Data
May 18, 2015  (EP) .................................. 15168025

(51) Int. Cl.
*A61K 39/00* (2006.01)
*A61K 39/39* (2006.01)
*A61P 35/00* (2006.01)

(52) U.S. Cl.
CPC ...... *A61K 39/001106* (2018.08); *A61K 39/39* (2013.01); *A61P 35/00* (2018.01); *A61K 2039/505* (2013.01); *A61K 2039/55516* (2013.01); *A61K 2039/55561* (2013.01); *A61K 2039/6031* (2013.01); *A61K 2039/622* (2013.01)

(58) Field of Classification Search
CPC ............ A61K 39/001106; A61K 39/39; A61K 2039/505; A61K 2039/55516; A61K 2039/55561; A61K 2039/6031; A61K 2039/622; A61P 35/00
See application file for complete search history.

(56) References Cited

U.S. PATENT DOCUMENTS

| | | | | |
|---|---|---|---|---|
| 9,636,415 B2* | 5/2017 | Mudde | ............... | C07K 14/4713 |
| 10,189,905 B2* | 1/2019 | Mudde | .................. | A61P 37/06 |
| 10,328,134 B2* | 6/2019 | Mudde | ........... | A61K 39/001144 |
| 10,434,170 B2* | 10/2019 | Mudde | .................... | A61P 37/08 |
| 2012/0108455 A1* | 5/2012 | Kodandapani | ..... | C07K 16/2863 506/9 |
| 2013/0243767 A1* | 9/2013 | Mudde | ............... | C07K 16/2896 424/134.1 |

FOREIGN PATENT DOCUMENTS

| | | | | |
|---|---|---|---|---|
| EP | 1844788 | | 10/2007 | |
| EP | 1844788 A1 | | 10/2007 | |
| WO | 2007098934 A1 | | 9/2007 | |
| WO | WO-2012066293 A1 | * | 5/2012 | ............. C07K 14/71 |
| WO | 2014009209 | | 1/2014 | |
| WO | 2014009209 A2 | | 1/2014 | |
| WO | 2014187743 A1 | | 11/2014 | |
| WO | WO-2014187743 A1 | * | 11/2014 | ......... A61K 39/0011 |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Rudikoff et al., Proc. Natl. Acad. Sci. USA, 79:1979-1983 (Year: 1982).*
Beckman et al., Cancer 109:170-179 (Year: 2007).*
Brennan et al. "HER2/Neu: mechanisms of dimerization/oligomerization." Oncogene 19: 6093-6101 (2000).
Franklin et al. "Insights into ErbB signaling from the structure of the ErbB2-pertuzumab complex." Cancer Cell vol. 5:4 pp. 317-328 (Apr. 2004).
Hartmann et al. "Rational design of new CpG oligonucleotides that combine B cell activation with high IFN-α induction in plasmacytoid dendritic cells." Eur. J. Immunol. 33:1633-1641 (2003).
International Search Report for corresponding International Patent Application No. PCT/EP2016/061035 dated Jul. 24, 2016.
International Written Opinion for corresponding International Patent Application No. PCT/EP2016/061035 dated Jul. 24, 2016.
H. Wei et al, "Targeted Delivery of Tumor Antigens to Activated Dendritic Cells via CD11c Molecules Induces Potent Antitumor Immunity in Mice," Clinical Cancer Research, vol. 15, No. 14, Jul. 15, 2009 (Jul. 15, 2009), pp. 4612-4621.
International Patent Application No. PCT/EP2016/061035, Written Opinion (dated Jul. 14, 2016).
International Patent Application No. PCT/EP2016/061035, Int'l Search Report (dated Jul. 14, 2016).
Abel et al. "Deoxycytidyl-Deoxyguanosine Oligonucleotide Classes A, B, and C Induce Distinct Cytokine Gene Expression Patterns in Rhesus Monkey Peripheral Blood Mononuclear Cells and Distinct Alpha Interferon Responses in TLR9-Expressing Rhesus Monkey Plasmacytoid Dendritic Cells." Clin. & Diag. Lab., 12(5):606-621 (May 2005).

(Continued)

*Primary Examiner* — Phuong Huynh
(74) *Attorney, Agent, or Firm* — Loza & Loza, LLP; Michael F. Fedrick

(57) ABSTRACT

The invention provides for an immunogenic composition comprising a. a directed adjuvant comprising at least an anti-CD32 moiety linked to a TLR9 ligand and a first peptidic alpha-helix; and b. an immunogen comprising an extracellular Her2/neu domain that is linked to a second peptidic alpha-helix coiled to the first alpha-helix; The invention further provides a kit for producing such immunogenic composition, a vaccine comprising such immunogenic composition and its medical use, such as for treating Her2/neu positive tumor diseases.

Figure 1:
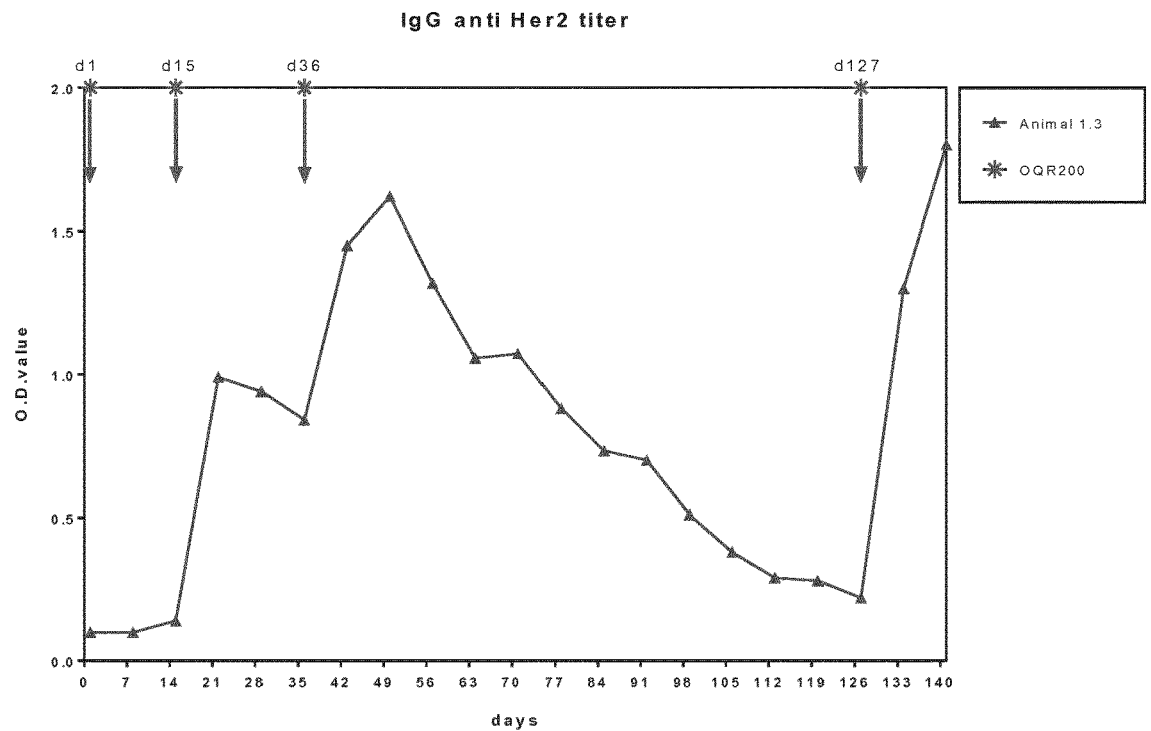

17 Claims, 8 Drawing Sheets
Specification includes a Sequence Listing.

(56) References Cited

OTHER PUBLICATIONS

Arndt et al. "Helix-stabilized fv (hsfv) antibody fragments: substituting the constant domains of a fab fragment for a heterodimeric coiled-coil domain." J. Mol. Biol., 312:21-228 (2001).
Berntzen et al. "Identification of a High Affinity FcγRIIA-binding peptide that distinguishes FcγRIIA from FcγRIIB and exploits FcγRIIA-mediated phagocytosis and degradation." J. Biol. Chem, 284(2):1126-1135 (Jan. 9, 2009).
Chao et al. "Use of a heterodimeric coiled-coil system for biosensor application and affinity purification." J. Chromatography B: Biomedical Sciences & Applications, vol. 715:1, pp. 307-329 (Sep. 11, 1998).
Cheever et al. "Provenge (Sipuleucel-T) in Prostate Cancer: The First FDA-Approved Therapeutic Cancer Vaccine." Clin. Cancer Res. 17(11):3520-3526 (Jun. 1, 2011).
Eaton-Bassiri et al. "Toll-like receptor 9 can be expressed at the cell surface of distinct populations of tonsils and human peripheral blood mononuclear cells." Infection & Immunity, 72(12):7202-7211 (Dec. 2004).
Greenman et al. "Characterization of a new monoclonal anti-Fcγ RII antibody, AT10, and its incorporation into a bispecific F(ab')2 derivative for recruitment of cytotoxic effectors." Molecular Immuno., 28(11):1243-1254 (Nov. 1991).
Krieg ete al. "CpG motifs in bacterial DNA trigger direct B-cell activation." Nature: Letters, 374:546-549 (Apr. 6, 1995).
Krug et al. "Identification of CpG oligonucleotide sequences with high induction of IFN-α/β in plasmacytoid dendritic cells." Eur. J. Immunol., 31:2154-2163 (2001).
Linley, "Tumour-associated antigens: considerations for their use in tumour immunotherapy." Int. J. Hematol., 93:263-273 (2011).
Litowski et al. "Designing heterodimeric two-stranded α-helical coiled-coils, effects of hydrophobicity and α-helical propensity on protein folding, stability, and specificity". J. Biol. Chem. 277(40):37272-37279 (Oct. 4, 2002).
Litowski et al. "Designing heterodimeric two-stranded α-helical coiled-coils: the effect of chain length on protein folding, stability and specificity." CJournal of Peptide Research, 58:477-492 (Dec. 2001).

MacIntyre et al. "Mechanism of human monocyte activation via the 40-kDa Fc receptor for IgG." J. Immunol., 141(12):4333-4343 (Dec. 15, 1988).
Mathis et al. "Back to central tolerance." Immunity, 20:509-516 (May 2004).
Milani et al. "Active immunotherapy in HER2 overexpressing breast cancer: current status and future perspectives." Annals of Oncology, 24(77):1740-1748 (Jul. 1, 2013).
Miller et al. "Peripheral T cell tolerance." Annu. Rev. Immunol., 10:51-69 (1992).
Puig et al. "TLR9 and TLR7 agonists mediate distinct type I IFN responses in humans and nonhuman primates in vitro and in vivo." J. Leukocyte Biol., 91(1):147-158 (Jan. 2012).
Saikh et al. "Human monocytes infected with yersinia pestis express cell surface TLR9 and differentiate into dendritic cell." J. Immunol., 173:7426-7434 (2004).
Stuart et al. "Isolation and expression of cDNA clones encoding a human receptor for IgG (Fc gamma RII)." J. Experimental Medicine 166(6):1668-1684 (Dec. 1, 1987).
Tafuri et al. "T cell awareness of paternal alloantigens during pregnancy." Science; Washington, vol. 270, 5236:630-633 (Oct. 27, 1995).
Tanaka et al. "Functional cell surface expression of Toll-like receptor 9 promotes cell proliferation and survival in human hepatocellular carcinomas." Int. J. Oncology 37:805-814 (2010).
Tel et al. "Targeted delivery of CpG ODN to CD32 on human and monkey plasmacytoid dendritic cells augments IFNα secretion." Immunobiol. 217:1017-1024 (2012).
Tversky et al. "Subcutaneous allergen immunotherapy restores human dendritic cell innate immune function." Clin. Exp. Allergy 40(1):94-102 (Jan. 2010).
Van Reijsen et al. "Skin-derived aeroallergen-specific T-cell clones of Th2 phenotype in patients with atopic dermatitis." J. Allergy & Clin. Immunol. 90:():184-193 (Aug. 1992).
Wei et al. "Targeted Delivery of Tumor Antigens to Activated Dendritic Cells via CD11c Molecules Induces Potent Antitumor Immunity in Mice." Clin. Cancer Res., 15:4612-4621 (Jul. 2009).

* cited by examiner

Fig. 5:

SEQ ID 1:

Amino acid-Sequence CyErb2 (Her2/neu from Cynomolgus monkeys)

```
1          10         20         30         40         50
TQVCTGTDMK LRLPASPETH LDMLRHLYQG CQVVQGNLEL TYLPTNASLS
51         60         70         80         90         100
FLQDIQEVQG YVLIAHNQVR QVPLQRLRIV RGTQLFEDNY ALAVLDNGNP
101        110        120        130        140        150
LNNTTPVTGA SPGGLRELQL RSLTEILKGG VLIQRNPQLC YQDTILWKDI
151        160        170        180        190        200
FHKNNQLALT LIDTNRSRAC HPCSPVCKGS RCWGESSEDC QSLTRTVCAG
201        210        220        230        240        250
GCARCKGPLP TDCCHEQCAA GCTGPKHSDC LACLHFNHSG ICELHCPALV
251        260        270        280        290        300
TYNTDTFESM PNPEGRYTFG ASCVTACPYN YLSTDVGSCT LVCPLHNQEV
301        310        320        330        340        350
TAEDGTQRCE KCSKPCARVC YGLGMEHLRE VRAVTSANIQ EFAGCKKIFG
351        360        370        380        390        400
SLAFLPESFD GDPASNTAPL QPEQLRVFET LEEITGYLYI SAWPDSLPDL
401        410        420        430        440        450
SVLQNLQVIR GRILHNGAYS LTLQGLGISW LGLRSLRELG SGLALIHHNT
451        460        470        480        490        500
RLCFVHTVPW DQLFRNPHQA LLHTANRPED ECVGEGLACH QLCARGHCWG
501        510        520        530        540        550
PGPTQCVNCS QFLRGQECVE ECRVLQGLPR EYVNARHCLP CHPECQPQNG
551        560        570        580        590        600
SVTCFGPEAD QCVACAHYKD PPFCVARCPS GVKPDLSYMP IWKFPDEEGT
601        610        620        630        640        650
CQSCPINCTH SCVDLDDKGC PAEQRASPLT
```

Fig. 5 continued

SEQ ID 2:

Amino acid-Sequence Erb2 (Her2/neu from humans)

```
1         10         20         30         40         50
TQVCTGTDMK LRLPASPETH LDMLRHLYQG CQVVQGNLEL TYLPTNASLS
51        60         70         80         90         100
FLQDIQEVQG YVLIAHNQVR QVPLQRLRIV RGTQLFEDNY ALAVLDNGDP
101       110        120        130        140        150
LNNTTPVTGA SPGGLRELQL RSLTEILKGG VLIQRNPQLC YQDTILWKDI
151       160        170        180        190        200
FHKNNQLALT LIDTNRSRAC HPCSPMCKGS RCWGESSEDC QSLTRTVCAG
201       210        220        230        240        250
GCARCKGPLP TDCCHEQCAA GCTGPKHSDC LACLHFNHSG ICELHCPALV
251       260        270        280        290        300
TYNTDTFESM PNPEGRYTFG ASCVTACPYN YLSTDVGSCT LVCPLHNQEV
301       310        320        330        340        350
TAEDGTQRCE KCSKPCARVC YGLGMEHLRE VRAVTSANIQ EFAGCKKIFG
351       360        370        380        390        400
SLAFLPESFD GDPASNTAPL QPEQLQVFET LEEITGYLYI SAWPDSLPDL
401       410        420        430        440        450
SVFQNLQVIR GRILHNGAYS LTLQGLGISW LGLRSLRELG SGLALIHHNT
451       460        470        480        490        500
HLCFVHTVPW DQLFRNPHQA LLHTANRPED ECVGEGLACH QLCARGHCWG
501       510        520        530        540        550
PGPTQCVNCS QFLRGQECVE ECRVLQGLPR EYVNARHCLP CHPECQPQNG
551       560        570        580        590        600
SVTCFGPEAD QCVACAHYKD PPFCVARCPS GVKPDLSYMP IWKFPDEEGA
601       610        620        630        640        650
CQPCPINCTH SCVDLDDKGC PAEQRASPLT
```

Fig. 5 continued

SEQ ID 3:

Amino acid sequence of ScFV-coil1

```
1         10         20         30         40         50
MELGLSWIFL LAILKGVQCE VQLQQSGPEL KKPGETVKIS CKASGYTFTN
51        60         70         80         90        100
YNWVKQAPGK GLKWMGWLNT YTGESIYPDD FKGRFAFSSE TSASTAYLQI
101       110        120        130        140        150
NNLKGMNEDM ATYFCARGDY GYDDPLDYWG QGTSVTVSSG GGGSGGGGSG
151       160        170        180        190        200
SGGGDIVMTQ AAPSVPVTPG ESVSISCRSS KSLLHTNGNT YLHWFLQRPG
201       210        220        230        240        250
QSPQLLIYRM SVLASGVPDR FSGSGSGTAF TLSISRVEAE DVGVFYCMQH
251       260        270        280        290        300
LEYPLTFGAG TKLELKGSIS AWSHPQFEKG PEVSALEKEV SALEKEVSAL
301       310
EKEVSALEKE VSALEK
```

AA 1-19: leader sequence (to secrete the product)
IAA 20-271 sequence of ScFV (the VH domain is underlined, Vl is double underlined) order of VH and VL domain may be swapped)
IAA140-154 Linker may be changed to any linker used in ScFV preparation
AA 272-279: StrepTag II for purification may be exchanged to any type of tag e.g. flag tag or HIS tag.
AA280-281: short linker (maybe longer)
AA282-316: heptad repeat alpha helix (pepE) to form the coiled coil with the counter heptad repeat alpha helix in the immunogen (pepK). In the example 5 repeats are used, more repeats may cause auto-aggregation and less repeats will reduce the affinity.

SEQ ID 4: linker

GGGSHHHHHHGGGSGG

SEQ ID 5: linker

GGGSGGGS

SEQ ID 6: TRL9 agonist CpG class A: ODN2216

GGGGGACGATCGTCGGGGGG

SEQ ID 7: TRL9 agonist CpG class B: ODN2006

TCGTCGTTTTGTCGTTTTGTCGTT

SEQ ID 8: TRL9 agonist CpG class C: ODNM362

TCGTCGTCGTTCGAACGACGTTGAT

Fig. 5 continued

SEQ ID 9:

Amino acid-Sequence CyErb2-coil (Her2/neu from Cynomolgus monkeys including pepK of the S-TIR technology)

```
1         10         20         30         40         50
TQVCTGTDMK LRLPASPETH LDMLRHLYQG CQVVQGNLEL TYLPTNASLS
51        60         70         80         90        100
FLQDIQEVQG YVLIAHNQVR QVPLQRLRIV RGTQLFEDNY ALAVLDNGNP
101       110        120        130        140        150
LNNTTPVTGA SPGGLRELQL RSLTEILKGG VLIQRNPQLC YQDTILWKDI
151       160        170        180        190        200
FHKNNQLALT LIDTNRSRAC HPCSPVCKGS RCWGESSEDC QSLTRTVCAG
201       210        220        230        240        250
GCARCKGPLP TDCCHEQCAA GCTGPKHSDC LACLHFNHSG ICELHCPALV
251       260        270        280        290        300
TYNTDTFESM PNPEGRYTFG ASCVTACPYN YLSTDVGSCT LVCPLHNQEV
301       310        320        330        340        350
TAEDGTQRCE KCSKPCARVC YGLGMEHLRE VRAVTSANIQ EFAGCKKIFG
351       360        370        380        390        400
SLAFLPESFD GDPASNTAPL QPEQLRVFET LEEITGYLYI SAWPDSLPDL
401       410        420        430        440        450
SVLQNLQVIR GRILHNGAYS LTLQGLGISW LGLRSLRELG SGLALIHHNT
451       460        470        480        490        500
RLCFVHTVPW DQLFRNPHQA LLHTANRPED ECVGEGLACH QLCARGHCWG
501       510        520        530        540        550
PGPTQCVNCS QFLRGQECVE ECRVLQGLPR EYVNARHCLP CHPECQPQNG
551       560        570        580        590        600
SVTCFGPEAD QCVACAHYKD PPFCVARCPS GVKPDLSYMP IWKFPDEEGT
601       610        620        630        640        650
CQSCPINCTH SCVDLDDKGC PAEQRASPLT GSGHHHHHHG GGSGG*KVSAL*
651       660        670        680
*KEKVSALKEK VSALKEKVSA LKEKVSALKE*
```

The linker between Her2 and pepK (italics) containing the HIS tag is underlined (GGGSHHHHHHGGGSGG, SEQ ID 4) may be replaced by any other linker e.g. GGGSGGGS, SEQ ID 5.

Fig. 5 continued

SEQ ID 10:

Amino acid-Sequence Erb2-coil (Her2/neu from humans including pepK of the S-TIR technology)

```
1          10         20         30         40         50
TQVCTGTDMK LRLPASPETH LDMLRHLYQG CQVVQGNLEL TYLPTNASLS
51         60         70         80         90         100
FLQDIQEVQG YVLIAHNQVR QVPLQRLRIV RGTQLFEDNY ALAVLDNGDP
101        110        120        130        140        150
LNNTTPVTGA SPGGLRELQL RSLTEILKGG VLIQRNPQLC YQDTILWKDI
151        160        170        180        190        200
FHKNNQLALT LIDTNRSRAC HPCSPMCKGS RCWGESSEDC QSLTRTVCAG
201        210        220        230        240        250
GCARCKGPLP TDCCHEQCAA GCTGPKHSDC LACLHFNHSG ICELHCPALV
251        260        270        280        290        300
TYNTDTFESM PNPEGRYTFG ASCVTACPYN YLSTDVGSCT LVCPLHNQEV
301        310        320        330        340        350
TAEDGTQRCE KCSKPCARVC YGLGMEHLRE VRAVTSANIQ EFAGCKKIFG
351        360        370        380        390        400
SLAFLPESFD GDPASNTAPL QPEQLQVFET LEEITGYLYI SAWPDSLPDL
401        410        420        430        440        450
SVFQNLQVIR GRILHNGAYS LTLQGLGISW LGLRSLRELG SGLALIHHNT
451        460        470        480        490        500
HLCFVHTVPW DQLFRNPHQA LLHTANRPED ECVGEGLACH QLCARGHCWG
501        510        520        530        540        550
PGPTQCVNCS QFLRGQECVE ECRVLQGLPR EYVNARHCLP CHPECQPQNG
551        560        570        580        590        600
SVTCFGPEAD QCVACAHYKD PPFCVARCPS GVKPDLSYMP IWKFPDEEGA
601        610        620        630        640        650
CQPCPINCTH SCVDLDDKGC PAEQRASPLT GSGHHHHHHG GSGG*KVSAL*
651        660        670        680
*KEKVSALKEK VSALKEKVSA LKEKVSALKE*
```

The linker between Her2 and pepK (italics) containing the HIS tag is underlined (GGGSHHHHHHGGGSGG, SEQ ID 4) may be replaced by any other linker e.g. GGGSGGGS, SEQ ID 5.

Fig. 5 continued

SEQ ID 38:

Amino acid-Sequence Erb2-coil (Her2/neu from humans including pepK of the S-TIR technology)

```
1          10         20         30         40         50
TQVCTGTDMK LRLPASPETH LDMLRHLYQG CQVVQGNLEL TYLPTNASLS
51         60         70         80         90        100
FLQDIQEVQG YVLIAHNQVR QVPLQRLRIV RGTQLFEDNY ALAVLDNGDP
101       110        120        130        140        150
LNNTTPVTGA SPGGLRELQL RSLTEILKGG VLIQRNPQLC YQDTILWKDI
151       160        170        180        190        200
FHKNNQLALT LIDTNRSRAC HPCSPMCKGS RCWGESSEDC QSLTRTVCAG
201       210        220        230        240        250
GCARCKGPLP TDCCHEQCAA GCTGPKHSDC LACLHFNHSG ICELHCPALV
251       260        270        280        290        300
TYNTDTFESM PNPEGRYTFG ASCVTACPYN YLSTDVGSCT LVCPLHNQEV
301       310        320        330        340        350
TAEDGTQRCE KCSKPCARVC YGLGMEHLRE VRAVTSANIQ EFAGCKKIFG
351       360        370        380        390        400
SLAFLPESFD GDPASNTAPL QPEQLQVFET LEEITGYLYI SAWPDSLPDL
401       410        420        430        440        450
SVFQNLQVIR GRILHNGAYS LTLQGLGISW LGLRSLRELG SGLALIHHNT
451       460        470        480        490        500
HLCFVHTVPW DQLFRNPHQA LLHTANRPED ECVGEGLACH QLCARGHCWG
501       510        520        530        540        550
PGPTQCVNCS QFLRGQECVE ECRVLQGLPR EYVNARHCLP CHPECQPQNG
551       560        570        580        590        600
SVTCFGPEAD QCVACAHYKD PPFCVARCPS GVKPDLSYMP IWKFPDEEGA
601       620        630        640        650        660
CQPCPINCTH SCVDLDDKGC PAEQRASPLT SSGGGSGGKV SALKEKVSAL
661       670        780
KEKVSALKEK VSALKEKVSA LKE
```

The linker between Her2 and pepK (italics) does not contain the HIS tag and is underlined (SEQ ID 39: SSGGGSGG) and may be replaced by any other linker consisting of G and S amino acid residues of e.g. 5-30 amino acid length, such as GGGSGGGS (SEQ ID 5).

SEQUENCE LISTING

```
<160> NUMBER OF SEQ ID NOS: 39

<210> SEQ ID NO 1
<211> LENGTH: 630
<212> TYPE: PRT
<213> ORGANISM: Macaca fascicularis
<220> FEATURE:
<223> OTHER INFORMATION: CyErb2

<400> SEQUENCE: 1

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asn Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Val
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300
```

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
            325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
            355                 360                 365

Pro Leu Gln Pro Glu Gln Leu Arg Val Phe Glu Thr Leu Glu Glu Ile
            370                 375                 380

Thr Gly Tyr Leu Tyr Ile Ser Ala Trp Pro Asp Ser Leu Pro Asp Leu
385                 390                 395                 400

Ser Val Leu Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
                435                 440                 445

Asn Thr Arg Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
            515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Thr Cys Gln Ser Cys Pro Ile Asn Cys
            595                 600                 605

Thr His Ser Cys Val Asp Leu Asp Asp Lys Gly Cys Pro Ala Glu Gln
610                 615                 620

Arg Ala Ser Pro Leu Thr
625                 630

<210> SEQ ID NO 2
<211> LENGTH: 630
<212> TYPE: PRT
<213> ORGANISM: Homo sapiens
<220> FEATURE:
<223> OTHER INFORMATION: Erb2

<400> SEQUENCE: 2

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

```
Val Val Gln Gly Asn Leu Glu Leu Thr Tyr Leu Pro Thr Asn Ala Ser
         35                  40                  45

Leu Ser Phe Leu Gln Asp Ile Gln Glu Val Gln Gly Tyr Val Leu Ile
 50                  55                  60

Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
                115                 120                 125

Gly Gly Val Leu Ile Gln Arg Asn Pro Gln Leu Cys Tyr Gln Asp Thr
            130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg Thr Val Cys Ala Gly Gly Cys Ala Arg Cys Lys Gly Pro
                195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
                260                 265                 270

Cys Val Thr Ala Cys Pro Tyr Asn Tyr Leu Ser Thr Asp Val Gly Ser
    275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
                340                 345                 350

Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
            435                 440                 445
```

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Cys Arg Val Leu Gln Gly Leu
        515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
610                 615                 620

Arg Ala Ser Pro Leu Thr
625                 630

<210> SEQ ID NO 3
<211> LENGTH: 316
<212> TYPE: PRT
<213> ORGANISM: Artificial Sequence
<220> FEATURE:
<223> OTHER INFORMATION: ScFV-coil1

<400> SEQUENCE: 3

Met Glu Leu Gly Leu Ser Trp Ile Phe Leu Leu Ala Ile Leu Lys Gly
1               5                   10                  15

Val Gln Cys Glu Val Gln Leu Gln Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Asn Trp Val Lys Gln Ala Pro Gly Lys Gly Leu Lys Trp
    50                  55                  60

Met Gly Trp Leu Asn Thr Tyr Thr Gly Glu Ser Ile Tyr Pro Asp Asp
65                  70                  75                  80

Phe Lys Gly Arg Phe Ala Phe Ser Ser Glu Thr Ser Ala Ser Thr Ala
                85                  90                  95

Tyr Leu Gln Ile Asn Asn Leu Lys Gly Met Asn Glu Asp Met Ala Thr
            100                 105                 110

Tyr Phe Cys Ala Arg Gly Asp Tyr Gly Tyr Asp Pro Leu Asp Tyr
        115                 120                 125

Trp Gly Gln Gly Thr Ser Val Thr Val Ser Ser Gly Gly Gly Ser
    130                 135                 140

Gly Gly Gly Gly Ser Gly Ser Gly Gly Asp Ile Val Met Thr Gln
145                 150                 155                 160

Ala Ala Pro Ser Val Pro Val Thr Pro Gly Glu Ser Val Ser Ile Ser
                165                 170                 175

```
Cys Arg Ser Ser Lys Ser Leu Leu His Thr Asn Gly Asn Thr Tyr Leu
            180                 185                 190

His Trp Phe Leu Gln Arg Pro Gly Gln Ser Pro Gln Leu Leu Ile Tyr
        195                 200                 205

Arg Met Ser Val Leu Ala Ser Gly Val Pro Asp Arg Phe Ser Gly Ser
    210                 215                 220

Gly Ser Gly Thr Ala Phe Thr Leu Ser Ile Ser Arg Val Glu Ala Glu
225                 230                 235                 240

Asp Val Gly Val Phe Tyr Cys Met Gln His Leu Glu Tyr Pro Leu Thr
                245                 250                 255

Phe Gly Ala Gly Thr Lys Leu Glu Leu Lys Gly Ser Ile Ser Ala Trp
            260                 265                 270

Ser His Pro Gln Phe Glu Lys Gly Pro Glu Val Ser Ala Leu Glu Lys
        275                 280                 285

Glu Val Ser Ala Leu Glu Lys Glu Val Ser Ala Leu Glu Lys Glu Val
    290                 295                 300

Ser Ala Leu Glu Lys Glu Val Ser Ala Leu Glu Lys
305                 310                 315

<210> SEQ ID NO 4
<211> LENGTH: 16
<212> TYPE: PRT
<213> ORGANISM: Artificial Sequence
<220> FEATURE:
<223> OTHER INFORMATION: linker

<400> SEQUENCE: 4

Gly Gly Gly Ser His His His His His His Gly Gly Gly Ser Gly Gly
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: linker

<400> SEQUENCE: 5

Gly Gly Gly Ser Gly Gly Gly Ser
1               5

<210> SEQ ID NO 6
<211> LENGTH: 20
<212> TYPE: DNA
<213> ORGANISM: Artificial Sequence
<220> FEATURE:
<223> OTHER INFORMATION: TRL9 agonist CpG class A

<400> SEQUENCE: 6 ggggacgat cgtcgggggg                                              20

<210> SEQ ID NO 7
<211> LENGTH: 24
<212> TYPE: DNA
<213> ORGANISM: Artificial Sequence
<220> FEATURE:
<223> OTHER INFORMATION: TRL9 agonist CpG class B

<400> SEQUENCE: 7
tcgtcgtttt gtcgttttgt cgtt                                        24

<210> SEQ ID NO 8
```

```
<211> LENGTH: 25
<212> TYPE: DNA
<213> ORGANISM: Artificial Sequence
<220> FEATURE:
<223> OTHER INFORMATION: TRL9 agonist CpG class C

<400> SEQUENCE: 8
tcgtcgtcgt tcgaacgacg ttgat                                     25

<210> SEQ ID NO 9
<211> LENGTH: 680
<212> TYPE: PRT
<213> ORGANISM: Artificial Sequence
<220> FEATURE:
<223> OTHER INFORMATION: CyErb2-coil

<400> SEQUENCE: 9
```

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asn Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Val
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

```
Tyr Gly Leu Gly Met Glu His Leu Arg Glu Val Arg Ala Val Thr Ser
            325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
            355                 360                 365

Pro Leu Gln Pro Glu Gln Leu Arg Val Phe Glu Thr Leu Glu Glu Ile
            370                 375                 380

Thr Gly Tyr Leu Tyr Ile Ser Ala Trp Pro Asp Ser Leu Pro Asp Leu
385                 390                 395                 400

Ser Val Leu Gln Asn Leu Gln Val Ile Arg Gly Arg Ile Leu His Asn
            405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
            435                 440                 445

Asn Thr Arg Leu Cys Phe Val His Thr Val Pro Trp Asp Gln Leu Phe
            450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Cys Arg Val Leu Gln Gly Leu
            515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Thr Cys Gln Ser Cys Pro Ile Asn Cys
            595                 600                 605

Thr His Ser Cys Val Asp Leu Asp Asp Lys Gly Cys Pro Ala Glu Gln
610                 615                 620

Arg Ala Ser Pro Leu Thr Gly Ser Gly His His His His His His Gly
625                 630                 635                 640

Gly Ser Gly Gly Lys Val Ser Ala Leu Lys Glu Lys Val Ser Ala
            645                 650                 655

Leu Lys Glu Lys Val Ser Ala Leu Lys Glu Lys Val Ser Ala Leu Lys
            660                 665                 670

Glu Lys Val Ser Ala Leu Lys Glu
            675                 680

<210> SEQ ID NO 10
<211> LENGTH: 680
<212> TYPE: PRT
<213> ORGANISM: Artificial Sequence
<220> FEATURE:
<223> OTHER INFORMATION: Erb2-coil

<400> SEQUENCE: 10
```

-continued

```
Thr Gln Val Cys Thr Gly Thr Asp Met Lys Leu Arg Leu Pro Ala Ser
 1               5                  10                  15

Pro Glu Thr His Leu Asp Met Leu Arg His Leu Tyr Gln Gly Cys Gln
                 20                  25                  30

Val Val Gln Gly Asn Leu Glu Leu Thr Tyr Leu Pro Thr Asn Ala Ser
                 35                  40                  45

Leu Ser Phe Leu Gln Asp Ile Gln Glu Val Gln Gly Tyr Val Leu Ile
 50                  55                  60

Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
                 100                 105                 110

Gly Gly Leu Arg Glu Leu Gln Leu Arg Ser Leu Thr Glu Ile Leu Lys
                 115                 120                 125

Gly Gly Val Leu Ile Gln Arg Asn Pro Gln Leu Cys Tyr Gln Asp Thr
                 130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                 165                 170                 175

Cys Lys Gly Ser Arg Cys Trp Gly Glu Ser Ser Glu Asp Cys Gln Ser
                 180                 185                 190

Leu Thr Arg Thr Val Cys Ala Gly Gly Cys Ala Arg Cys Lys Gly Pro
                 195                 200                 205

Leu Pro Thr Asp Cys Cys His Glu Gln Cys Ala Ala Gly Cys Thr Gly
                 210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                 245                 250                 255

Phe Glu Ser Met Pro Asn Pro Glu Gly Arg Tyr Thr Phe Gly Ala Ser
                 260                 265                 270

Cys Val Thr Ala Cys Pro Tyr Asn Tyr Leu Ser Thr Asp Val Gly Ser
                 275                 280                 285

Cys Thr Leu Val Cys Pro Leu His Asn Gln Glu Val Thr Ala Glu Asp
                 290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                 325                 330                 335

Ala Asn Ile Gln Glu Phe Ala Gly Cys Lys Lys Ile Phe Gly Ser Leu
                 340                 345                 350

Ala Phe Leu Pro Glu Ser Phe Asp Gly Asp Pro Ala Ser Asn Thr Ala
                 355                 360                 365

Pro Leu Gln Pro Glu Gln Leu Gln Val Phe Glu Thr Leu Glu Glu Ile
                 370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                 405                 410                 415
```

-continued

```
Gly Ala Tyr Ser Leu Thr Leu Gln Gly Leu Gly Ile Ser Trp Leu Gly
                420                 425                 430

Leu Arg Ser Leu Arg Glu Leu Gly Ser Gly Leu Ala Leu Ile His His
            435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
610                 615                 620

Arg Ala Ser Pro Leu Thr Gly Ser Gly His His His His His His Gly
625                 630                 635                 640

Gly Gly Ser Gly Gly Lys Val Ser Ala Leu Lys Glu Lys Val Ser Ala
                645                 650                 655

Leu Lys Glu Lys Val Ser Ala Leu Lys Glu Lys Val Ser Ala Leu Lys
            660                 665                 670

Glu Lys Val Ser Ala Leu Lys Glu
        675                 680

<210> SEQ ID NO 11
<211> LENGTH: 5
<212> TYPE: PRT
<213> ORGANISM: Artificial Sequence
<220> FEATURE:
<223> OTHER INFORMATION: peptide

<400> SEQUENCE: 11

Glu Val Ser Ala Leu
1               5

<210> SEQ ID NO 12
<211> LENGTH: 5
<212> TYPE: PRT
<213> ORGANISM: Artificial Sequence
<220> FEATURE:
<223> OTHER INFORMATION: peptide

<400> SEQUENCE: 12

Lys Val Ser Ala Leu
1               5

<210> SEQ ID NO 13
```

```
<211> LENGTH: 35
<212> TYPE: PRT
<213> ORGANISM: Artificial Sequence
<220> FEATURE:
<223> OTHER INFORMATION: peptide

<400> SEQUENCE: 13

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys Glu Val Ser Ala
            20                  25                  30

Leu Glu Lys
        35

<210> SEQ ID NO 14
<211> LENGTH: 35
<212> TYPE: PRT
<213> ORGANISM: Artificial Sequence
<220> FEATURE:
<223> OTHER INFORMATION: peptide

<400> SEQUENCE: 14

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu Lys Val Ser Ala
            20                  25                  30

Leu Lys Glu
        35

<210> SEQ ID NO 15
<211> LENGTH: 5
<212> TYPE: PRT
<213> ORGANISM: Artificial Sequence
<220> FEATURE:
<223> OTHER INFORMATION: peptide

<400> SEQUENCE: 15

Glu Ile Ala Ala Leu
1               5

<210> SEQ ID NO 16
<211> LENGTH: 5
<212> TYPE: PRT
<213> ORGANISM: Artificial Sequence
<220> FEATURE:
<223> OTHER INFORMATION: peptide

<400> SEQUENCE: 16

Lys Ile Ala Ala Leu
1               5

<210> SEQ ID NO 17
<211> LENGTH: 5
<212> TYPE: PRT
<213> ORGANISM: Artificial Sequence
<220> FEATURE:
<223> OTHER INFORMATION: peptide

<400> SEQUENCE: 17

Glu Ile Ser Ala Leu
1               5

<210> SEQ ID NO 18
<211> LENGTH: 5
<212> TYPE: PRT
```

```
<213> ORGANISM: Artificial Sequence
<220> FEATURE:
<223> OTHER INFORMATION: peptide

<400> SEQUENCE: 18

Lys Ile Ser Ala Leu
1               5

<210> SEQ ID NO 19
<211> LENGTH: 5
<212> TYPE: PRT
<213> ORGANISM: Artificial Sequence
<220> FEATURE:
<223> OTHER INFORMATION: peptide

<400> SEQUENCE: 19

Glu Val Ala Ala Leu
1               5

<210> SEQ ID NO 20
<211> LENGTH: 5
<212> TYPE: PRT
<213> ORGANISM: Artificial Sequence
<220> FEATURE:
<223> OTHER INFORMATION: peptide

<400> SEQUENCE: 20

Lys Val Ala Ala Leu
1               5

<210> SEQ ID NO 21
<211> LENGTH: 21
<212> TYPE: PRT
<213> ORGANISM: Artificial Sequence
<220> FEATURE:
<223> OTHER INFORMATION: peptide

<400> SEQUENCE: 21

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 22
<211> LENGTH: 28
<212> TYPE: PRT
<213> ORGANISM: Artificial Sequence
<220> FEATURE:
<223> OTHER INFORMATION: peptide

<400> SEQUENCE: 22

Glu Ile Ala Ala Leu Glu Lys Glu Ile Ala Ala Leu Glu Lys Glu Ile
1               5                   10                  15

Ala Ala Leu Glu Lys Glu Ile Ala Ala Leu Glu Lys
            20                  25

<210> SEQ ID NO 23
<211> LENGTH: 21
<212> TYPE: PRT
<213> ORGANISM: Artificial Sequence
<220> FEATURE:
<223> OTHER INFORMATION: peptide

<400> SEQUENCE: 23

Lys Ile Ala Ala Leu Lys Glu Lys Ile Ala Ala Leu Lys Glu Lys Ile
1               5                   10                  15
```

Ala Ala Leu Lys Glu
            20

<210> SEQ ID NO 24
<211> LENGTH: 28
<212> TYPE: PRT
<213> ORGANISM: Artificial Sequence
<220> FEATURE:
<223> OTHER INFORMATION: peptide

<400> SEQUENCE: 24

Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu
            20                  25

<210> SEQ ID NO 25
<211> LENGTH: 21
<212> TYPE: PRT
<213> ORGANISM: Artificial Sequence
<220> FEATURE:
<223> OTHER INFORMATION: peptide

<400> SEQUENCE: 25

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 26
<211> LENGTH: 28
<212> TYPE: PRT
<213> ORGANISM: Artificial Sequence
<220> FEATURE:
<223> OTHER INFORMATION: peptide

<400> SEQUENCE: 26

Glu Ile Ser Ala Leu Glu Lys Glu Ile Ser Ala Leu Glu Lys Glu Ile
1               5                   10                  15

Ser Ala Leu Glu Lys Glu Ile Ser Ala Leu Glu Lys
            20                  25

<210> SEQ ID NO 27
<211> LENGTH: 21
<212> TYPE: PRT
<213> ORGANISM: Artificial Sequence
<220> FEATURE:
<223> OTHER INFORMATION: peptide

<400> SEQUENCE: 27

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 28
<211> LENGTH: 28
<212> TYPE: PRT
<213> ORGANISM: Artificial Sequence
<220> FEATURE:
<223> OTHER INFORMATION: peptide

<400> SEQUENCE: 28

Lys Ile Ser Ala Leu Lys Glu Lys Ile Ser Ala Leu Lys Glu Lys Ile

```
1               5                   10                  15
Ser Ala Leu Lys Glu Lys Ile Ser Ala Leu Lys Glu
            20                  25

<210> SEQ ID NO 29
<211> LENGTH: 21
<212> TYPE: PRT
<213> ORGANISM: Artificial Sequence
<220> FEATURE:
<223> OTHER INFORMATION: peptide

<400> SEQUENCE: 29

Glu Val Ala Ala Leu Glu Lys Glu Val Ala Ala Leu Glu Lys Glu Val
1               5                   10                  15

Ala Ala Leu Glu Lys
            20

<210> SEQ ID NO 30
<211> LENGTH: 28
<212> TYPE: PRT
<213> ORGANISM: Artificial Sequence
<220> FEATURE:
<223> OTHER INFORMATION: peptide

<400> SEQUENCE: 30

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 31
<211> LENGTH: 21
<212> TYPE: PRT
<213> ORGANISM: Artificial Sequence
<220> FEATURE:
<223> OTHER INFORMATION: peptide

<400> SEQUENCE: 31

Lys Val Ala Ala Leu Lys Glu Lys Val Ala Ala Leu Lys Glu Lys Val
1               5                   10                  15

Ala Ala Leu Lys Glu
            20

<210> SEQ ID NO 32
<211> LENGTH: 28
<212> TYPE: PRT
<213> ORGANISM: Artificial Sequence
<220> FEATURE:
<223> OTHER INFORMATION: peptide

<400> SEQUENCE: 32

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 33
<211> LENGTH: 21
<212> TYPE: PRT
<213> ORGANISM: Artificial Sequence
<220> FEATURE:
<223> OTHER INFORMATION: peptide

<400> SEQUENCE: 33
```

-continued

Glu Val Ser Ala Leu Glu Lys Glu Val Ser Ala Leu Glu Lys Glu Val
1               5                   10                  15

Ser Ala Leu Glu Lys
            20

<210> SEQ ID NO 34
<211> LENGTH: 28
<212> TYPE: PRT
<213> ORGANISM: Artificial Sequence
<220> FEATURE:
<223> OTHER INFORMATION: peptide

<400> SEQUENCE: 34

Glu Val Ser Ala Leu Glu Lys Glu Val Ser Ala Leu Glu Lys Glu Val
1               5                   10                  15

Ser Ala Leu Glu Lys Glu Val Ser Ala Leu Glu Lys
            20                  25

<210> SEQ ID NO 35
<211> LENGTH: 21
<212> TYPE: PRT
<213> ORGANISM: Artificial Sequence
<220> FEATURE:
<223> OTHER INFORMATION: peptide

<400> SEQUENCE: 35

Lys Val Ser Ala Leu Lys Glu Lys Val Ser Ala Leu Lys Glu Lys Val
1               5                   10                  15

Ser Ala Leu Lys Glu
            20

<210> SEQ ID NO 36
<211> LENGTH: 28
<212> TYPE: PRT
<213> ORGANISM: Artificial Sequence
<220> FEATURE:
<223> OTHER INFORMATION: peptide

<400> SEQUENCE: 36

Lys Val Ser Ala Leu Lys Glu Lys Val Ser Ala Leu Lys Glu Lys Val
1               5                   10                  15

Ser Ala Leu Lys Glu Lys Val Ser Ala Leu Lys Glu
            20                  25

<210> SEQ ID NO 37
<211> LENGTH: 19
<212> TYPE: PRT
<213> ORGANISM: Artificial Sequence
<220> FEATURE:
<223> OTHER INFORMATION: peptide

<400> SEQUENCE: 37

Ala Asp Gly Ala Trp Ala Trp Val Trp Leu Thr Glu Thr Ala Val Gly
1               5                   10                  15

Ala Ala Lys

<210> SEQ ID NO 38
<211> LENGTH: 673
<212> TYPE: PRT
<213> ORGANISM: Artificial Sequence
<220> FEATURE:
<223> OTHER INFORMATION: Erb2-coil

<400> SEQUENCE: 38

```
Thr Gln Val Cys Thr Gly Thr Asp Met Lys Leu Arg Leu Pro Ala Ser
  1               5                  10                  15

Pro Glu Thr His Leu Asp Met Leu Arg His Leu Tyr Gln Gly Cys Gln
             20                  25                  30

Val Val Gln Gly Asn Leu Glu Leu Thr Tyr Leu Pro Thr Asn Ala Ser
             35                  40                  45

Leu Ser Phe Leu Gln Asp Ile Gln Glu Val Gln Gly Tyr Val Leu Ile
     50                  55                  60

Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
             115                 120                 125

Gly Gly Val Leu Ile Gln Arg Asn Pro Gln Leu Cys Tyr Gln Asp Thr
            130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
            195                 200                 205

Leu Pro Thr Asp Cys Cys His Glu Gln Cys Ala Ala Gly Cys Thr Gly
            210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
            290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
            370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
```

```
                420             425             430
Leu Arg Ser Leu Arg Glu Leu Gly Ser Gly Leu Ala Leu Ile His His
            435             440             445

Asn Thr His Leu Cys Phe Val His Thr Val Pro Trp Asp Gln Leu Phe
    450             455             460

Arg Asn Pro His Gln Ala Leu Leu His Thr Ala Asn Arg Pro Glu Asp
465             470             475             480

Glu Cys Val Gly Glu Gly Leu Ala Cys His Gln Leu Cys Ala Arg Gly
                485             490             495

His Cys Trp Gly Pro Gly Pro Thr Gln Cys Val Asn Cys Ser Gln Phe
            500             505             510

Leu Arg Gly Gln Glu Cys Val Glu Glu Cys Arg Val Leu Gln Gly Leu
            515             520             525

Pro Arg Glu Tyr Val Asn Ala Arg His Cys Leu Pro Cys His Pro Glu
            530             535             540

Cys Gln Pro Gln Asn Gly Ser Val Thr Cys Phe Gly Pro Glu Ala Asp
545             550             555             560

Gln Cys Val Ala Cys Ala His Tyr Lys Asp Pro Pro Phe Cys Val Ala
                565             570             575

Arg Cys Pro Ser Gly Val Lys Pro Asp Leu Ser Tyr Met Pro Ile Trp
            580             585             590

Lys Phe Pro Asp Glu Glu Gly Ala Cys Gln Pro Cys Pro Ile Asn Cys
            595             600             605

Thr His Ser Cys Val Asp Leu Asp Asp Lys Gly Cys Pro Ala Glu Gln
            610             615             620

Arg Ala Ser Pro Leu Thr Ser Ser Gly Gly Gly Ser Gly Gly Lys Val
625             630             635             640

Ser Ala Leu Lys Glu Lys Val Ser Ala Leu Lys Glu Lys Val Ser Ala
                645             650             655

Leu Lys Glu Lys Val Ser Ala Leu Lys Glu Lys Val Ser Ala Leu Lys
            660             665             670

Glu

<210> SEQ ID NO 39
<211> LENGTH: 8
<212> TYPE: PRT
<213> ORGANISM: Artificial Sequence
<220> FEATURE:
<223> OTHER INFORMATION: linker

<400> SEQUENCE: 39

Ser Ser Gly Gly Gly Ser Gly Gly
1               5
```

HER2/NEU IMMUNOGENIC COMPOSITION

CROSS-REFERENCE TO RELATED APPLICATIONS

This application is the U.S. national stage of International Patent Application No. PCT/EP2016/061035, filed on May 17, 2016 and entitled HER2/NEU IMMUNOGENIC COMPOSITION, which claims the benefit of priority under 35 U.S.C. § 119 from European Patent Application No. 15168025.3, filed May 18, 2015. The disclosures of the foregoing applications are incorporated herein by reference in their entirety.

SEQUENCE LISTING

The entire content of a Sequence Listing titled "Sequence_Listing.txt," created on Nov. 7, 2017 and having a size of 38 kilobytes, which has been submitted in electronic form in connection with the present application, is hereby incorporated by reference herein in its entirety.

The invention refers to immunogenic compositions comprising a Her2/neu immunogen and an anti-CD32 moiety linked to a TLR9 ligand, a vaccine comprising such immunogenic composition and its use in treating Her2/neu positive tumor disease conditions.

BACKGROUND

Cancer known medically as a malignant neoplasm, is a broad group of various diseases, all involving unregulated cell growth. In cancer, cells divide and grow uncontrollably, forming malignant tumors, and invade nearby parts of the body. The cancer may also spread to more distant parts of the body through the lymphatic system or bloodstream. Not all tumors are cancerous. Benign tumors do not grow uncontrollably, do not invade neighboring tissues, and do not spread throughout the body. There are over 200 different known cancers that afflict humans.

Determining what causes cancer is complex. Many things are known to increase the risk of cancer, including tobacco use, certain infections, radiation, lack of physical activity, obesity, and environmental pollutants. These can directly damage genes or combine with existing genetic faults within cells to cause the disease. Approximately five to ten percent of cancers are entirely hereditary.

Cancer can be detected in a number of ways, including the presence of certain signs and symptoms, screening tests, or medical imaging. Once a possible cancer is detected it is diagnosed by microscopic examination of a tissue sample. Cancer is usually treated with chemotherapy, radiation therapy and surgery. The chances of surviving the disease vary greatly by the type and location of the cancer and the extent of disease at the start of treatment. While cancer can affect people of all ages, and a few types of cancer are more common in children, the risk of developing cancer generally increases with age. In 2007, cancer caused about 13% of all human deaths worldwide (7.9 million). Rates are rising as more people live to an old age and as mass lifestyle changes occur in the developing world.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control.

Immune tolerance or immunological tolerance is the process by which the immune system does not attack an antigen. In natural or self-tolerance, the body does not mount an immune response to self-antigens. It occurs in three forms: central tolerance, peripheral tolerance and acquired tolerance Central Tolerance[1]:

Central tolerance occurs during lymphocyte development and operates in the thymus and bone marrow. Here, T and B lymphocytes that recognize self-antigens are deleted before they develop into fully immunocompetent cells, preventing autoimmunity. This process is most active in fetal life, but continues throughout life as immature lymphocytes are generated.

Peripheral Tolerance[2]:

Peripheral tolerance is immunological tolerance developed after T and B cells mature and enter the periphery. The T cells that leave the thymus are relatively but not completely safe. Some will have receptors (TCRs) that can respond to self-antigens that are present in such high concentration that they can bind to "weak" receptors the T cell did not encounter in the thymus (such as, tissue-specific molecules like those in the islets of Langerhans, brain or spinal cord) Those self-reactive T cells that escape intrathymic negative selection in the thymus can inflict cell injury unless they are deleted or effectively muzzled in the peripheral tissue. Several feedback mechanism to silence such potentially auto reactive T cells are known to exist. They include following: Anergy, Activation-induced cell death, Peripheral suppression Acquired or Induced Tolerance[3]:

Acquired or induced tolerance refers to the immune system's adaptation to external antigens characterized by a specific non-reactivity of the lymphoid tissues to a given antigen that in other circumstances would likely induce cell-mediated or humoral immunity. One of the most important natural kinds of acquired tolerance is immune tolerance in pregnancy, where the fetus and the placenta must be tolerated by the maternal immune system.

Immunotherapy Targeting Tumor Associated Antigens:

Cancer immunotherapy is the use of the immune system to reject cancer. The main premise is stimulating the patient's immune system to attack the malignant tumor cells that are responsible for the disease. This can be either through active immunization of the patient (e.g., by administering a cellular cancer vaccine, such as Provenge, Dendreon, Seattle, Wash., US)[4], in which case the patient's own immune system is trained to recognize tumor cells as targets to be destroyed, or through the administration of therapeutic antibodies as drugs, in which case the patient's immune system is recruited to destroy tumor cells by the therapeutic antibodies. Another approach for activating the patient's immune system against tumors is to make use of so called tumor associated antigens (TAA's), which are self-proteins which are to some extend expressed on healthy normal cells, but overexpressed on tumor cells[5]. These TAAs are formulated and presented to the body in an immunogenic fashion such that the immune system will build a response despite the fact that these proteins are self. Obviously this approach will only be useful for TAAs against which the patient has developed peripheral or acquired tolerance. When the T and B cells recognizing the TAA have been deleted from the immunological repertoire, active cancer immunotherapy is not an option.

Breast cancer is a type of cancer originating from breast tissue of humans and other mammals. Worldwide, breast cancer comprises 23% of all cancers in women. In 2008, breast cancer caused 458,503 deaths worldwide (13.7% of cancer deaths in women). Breast cancers are classified by several grading systems (histopathology, Grade, Stage, Receptor status such as Her2 positive). Breast cancer is usually treated with surgery and then possibly with chemotherapy and/or radiation.

"Her2 positive" breast cancer (about 30% of breast cancer) is one of the Her2/neu positive tumor diseases. Further Her2/neu positive tumor diseases are ovarian, stomach, uterine, colorectal and non-small cell lung cancer.

Her2/neu:

The neu (ERBB2) gene encodes HER2 (Human Epidermal Growth Factor Receptor 2), a 185-kDa transmembrane glycoprotein, referred to as p185, HER2/neu, Her2, or erbB-2, possessing intrinsic protein tyrosine kinase activity. The receptor consists of an extracellular domain, with four subdomains (I-IV) including two cysteine rich domains, a transmembrane domain, and an intracellular domain, consisting of a juxtamembrane region, a tyrosine kinase domain, and a carboxyl tail harboring autophosphorylation sites. HER2/neu is homologous to, but distinct from, other members of the erbB family, which includes the epidermal growth factor receptor (EGFR or erbB-1), erbB-3, and erbB-4. The binding of cognate growth factors to these receptors regulates cell growth, proliferation, and differentiation through the activation of receptor tyrosine kinases, triggering an incompletely defined signal transduction cascade.

Some peptides of 10-30 aa in the extracellular domain of Her2/neu (23-652 aa) are part of a peptide vaccine as single or multiple peptides (E75, GP2, AE37 & NeuVax). The intracellular domain (676-1255 aa) is also a target of some vaccines.

Milani et al.[25] reviews active immunotherapy in Her2 overexpressing breast cancer. Besides peptide vaccines, a protein based vaccine based on the Her2 intracellular domain is described. Further, a dHER2 (truncated recombinant HER2 extracellular domain and intracellular domain) has been tested in 45 patients. Antibodies have developed only after four immunizations.

Vaccine Structure

WO2014/009209 A2 describes an immunoregulatory vaccine based on an immunogen and a directed adjuvant linked thereto. In particular, a vaccine is described which comprises an immunogenic composition comprising a directed adjuvant comprising at least an anti-CD32 moiety linked to a TLR9 ligand, and an immunogen, which is bound to the directed adjuvant, for use in treating a subject for eliciting a transient IgG immune response directed to the immunogen. The disclosure refers to an immunogen that is or comprises an antigen or epitope of a self-antigen, e.g. selected from the group consisting of a tumor associated antigen (TAA), preferably a tumor cell surface receptor or a soluble antigen produced by the tumor cell, such as Her2/neu, gastrin, interferon alpha (INFα), epidermal growth factor (EGF), EGF receptor (EGF-R), epithelial cell adhesion molecule (EpCAM), alphafetoprotein (AFP), carcinoembryonic antigen (CEA), MUC-1 or LewisY, prehormones and hormones, such as any of the digestive hormones, including secretin or insulin, thyroid hormones, or sexual hormones. As an example, a vaccine comprising a peptide immunogen (G17) is produced, for use in active immunotherapy in gastric cancer (see also WO2014/187743 A1).

WO2007098934A1 describes molecules capable of binding to TLR9 and to CD32 comprising at least one epitope of at least one antigen, its production and its use in a medicament, especially for the treatment of allergies.

Immune Balance:

The immune balance regulated by Th1/Th2/Th17/Treg cells plays a significant part in the development of immune therapies.

Th1 cells, (Type 1 helper T cells) are characterized by the production of proinflammatory cytokines like IFN-γ, IL-2, and TNF-β. Th1 cells are involved in cell-mediated immunity. The cytokines produced by Th1 cells stimulate the phagocytosis and destruction of microbial pathogens. Several chronic inflammatory diseases have been described as Th1 dominant diseases i.e. multiple sclerosis, diabetes, and rheumatoid arthritis.

Th2 cells (Type 2 helper T cells) are characterized by the production of IL-4, IL-5, IL-9, IL-10, and IL-13. Th2 cells are thought to play a role in allergy responses. Cytokines like IL-4 generally stimulate the production of antibodies. IL-5 stimulates eosinophil responses, also part of the immune response. Atopy and allergy are thought to be Th2 dominant conditions.

The imbalance of Th1/Th2 or Th17/Treg immunity becomes the cause of various immune diseases.

The Role of TLR9:

Toll-like receptors (TLRs) are a class of proteins that play a key role in the innate immune system. They are single, membrane-spanning, non-catalytic receptors usually expressed on the cell surface and in the endocytic compartment of sentinel cells such as macrophages and dendritic cells. TLR's recognize pathogen-associated molecular patterns (PAMPs), structurally conserved molecules, derived from microbes and initiate signalling to induce production of cytokines necessary for the innate immunity and subsequent adaptive immunity.

The various TLRs exhibit different patterns of expression. This gene is preferentially expressed in immune cell rich tissues, such as spleen, lymph node, bone marrow and peripheral blood leukocytes.

Thirteen TLRs (named simply TLR1 to TLR13) have been identified in humans and mice together, and equivalent forms of many of these have been found in other mammalian species. However, not every TLR receptor in mice is also found in humans or vice versa. In addition, not for every TLR receptor the ligand and function is known, e.g. TLR10 is orphan receptor with unknown function.

Activation of TLR receptors has been used for the treatment of various diseases e.g activation of TLR9 by pharmaceutical products has been shown to be beneficial in treatment of allergy and oncology. Studies in mice and human indicate that the natural ligands of TLR9 are unmethylated CpG sequences in DNA molecules. CpG sites are relatively rare (~1%) on vertebrate genomes in comparison to bacterial genomes or viral DNA. TLR9 is expressed by numerous cells of the immune system such as dendritic cells, B lymphocytes, monocytes and natural killer (NK) cells. However in healthy humans the TLR9 is expression is restricted to plasmacytoid dendritic cells (pDCs) and B cells. The expression is intracellularly, within the endosomal compartments and functions to alert the immune system of viral and bacterial infections by binding to DNA rich in CpG motifs. However under pathologiocal conditions TLR9 expression has been reported on the cell surface of cells as well[6-8].

Many different synthetic TLR9 agonist molecules have been reported. The agonistic ligands (TLR9 activating) have been classified into three groups:

The group consisting of CpG class A, in particular CpG-A (D)[9] oligodeoxynucleotides (ODN), also known as "D"-type ODN. Such TLR9 agonists induce a strong IFNa induction and minimal maturation of dendritic cells, and are herein called "group 1" TLR9 ligand. An example is ODN2216[10]:

GGGGGACGATCGTCGGGGGG (SEQ ID 6)

The group consisting of CpG class B, in particular CpG-B (K)[9] oligodeoxynucleotides (ODN), also known as "K"-type ODN. Such TLR9 agonists induce a weak IFNa induction and maturation of dendritic cells, and are herein called "group 2" TLR9 ligand. An example is ODN2006[11;12]:

TCGTCGTTTTGTCGTTTTGTCGTT (SEQ ID 7)

The group consisting of CpG class C, also known as CpG-C[9] oligodeoxynucleotides (ODN). Such TLR9 agonists induce IFNa and maturation of immature dendritic cells, and are herein called "group 3" TLR9 ligand. An example is ODNM362[9]:

TCGTCGTCGTTCGAACGACGTTGAT (SEQ ID 8)

All of the ligands for TLR9 described to date are based on nucleotides. Although antibodies specific for TLR9 have been reported and used to demonstrate the presence and location of the receptor, these molecules have not been described as ligands for TLR9, there was no report of any TLR9 activating or inhibiting activity.

The Role of CD32:

CD32 is strongly expressed on monocytes/dendritic cells and B cells and thus such molecules are designed to direct the immune response to these important immunological cells, with the intention to prevent antigen presentation by the B cells, while promoting antigen presentation by especially dendritic cells (DCs), the latter leads to induction of Th1 responses against the antigen, when sufficiently stimulated. There are at least two types of DCs: myeloid (mDC) and plasmacytoid dendritic cells (pDC), which has led to the new concept of DC1 and DC2 cells. In this concept DC1 cells promote the induction of Th1 cell development after antigen specific stimulation and DC2 cells support the development of Th2 cells. Monocyte derived DC (or mDC) are generally considered to be of DC1 type, whereas pDC are considered to be DC2 type. Both types of DC express CD32a and will induce an antigen specific T cell response; however it is not guaranteed that the outcome will be of Th1 type. In fact, in allergic donors Th2 responses are more likely. Importantly, the pDC express the TLR9 receptor, which binds CpG-ODNs (oligodeoxynucleotides (ODNs) containing unmethylated CpG motifs). Activation of this receptor in the pDC leads to a very strong production of IFN-alpha and IL-12, which promotes Th1 induction and thus transforms the potential DC2 into DC1 cells.

Thus, such molecules can combine the activation of the TLR9 receptor in pDC with the specific stimulation and induction of antigen specific Th1 cells.

In tumor immunotherapies there is the particular goal to use tumor antigen specific T helper type 1 (Th1) cells in addition to cytotoxic T lymphocytes (CTL).

Coiled Coils:

Coiled coils are consisting of structural motifs in proteins, in which 2-7 alpha-helices are coiled together like the strands of a rope; dimers and trimers are the most common types. The coiled coil helixes have been used to stabilize Fv antibody fragments resulting in heterodimeric coiled-coil domains[13].

SUMMARY OF THE INVENTION

There is a need to provide improved immunotherapies targeting Her2/neu and Her/2 neu dependent disease conditions. It is thus the object of the invention to provide a vaccine with improved immunogenicity, stability and structure to regulate the immune response to specific Her2/neu epitopes.

The object is solved by the subject matter as claimed.

According to the invention there is provided an immunogenic composition comprising the components
  a. a directed adjuvant comprising at least an anti-CD32 moiety linked to a TLR9 ligand and a first peptidic alpha-helix; and
  b. an immunogen comprising an extracellular Her2/neu domain that is linked to a second peptidic alpha-helix coiled to the first alpha-helix.

Specifically, said Her2/neu domain comprises or consists of
  a. a polypeptide identified by the amino acid sequence SEQ ID 1 or SEQ ID 2;
  b. a polypeptide which is a fragment of a. comprising at least one subdomain selected from the group consisting of subdomains I, II, III, and IV, preferably comprising at least any of the subdomain domains IV or III or II;
  c. a polypeptide which is a fragment of a. comprising at least two subdomains selected from the group consisting of subdomains I, II, III, and IV, preferably comprising
    i) at least the subdomain IV and any of III, II or I; or
    ii) at least the subdomain III and any of IV, II or I;
  d. a polypeptide with at least 75% sequence identify to any of a. to c., preferably at least 80%, or at least 85%, or at least 90%, or at least 95% sequence identify.

Specifically, said Her2/neu domain comprises both, B-cell epitopes and T-ce4ll epitopes, to elicit B-cell and T-cell immune response. Specifically, the immune response is reversible, even when T-cell immunity is induced, indicating the absence of treatment induced autoimmune disease.

Specifically, said Her2/neu domain is present in the immunogenic composition as a monomer, avoiding unspecific aggregation of Her2/neu domains, in particular avoiding an undesired content of free Her2/neu domains, i.e. those which are not bound by covalent linkage or fusion, but would have a tendency of oligomerizing with other Her2/neu domains through electrostatic or hydrophobic interaction. Specifically, formation of a dimer or oligomer of Her2/neu domains without being covalently linked or fused to the peptidic alpha-helix is avoided. Thus, excess Her2/neu domains that are not part of the immunogen and not linked to a second peptidic alpha-helix are preferably not comprised in the immunogenic composition.

Specifically, each of said first and second alpha-helices comprises 2-9 amino acid repeats of an amino acid motif, wherein the alpha-helices specifically bind to each other with a Kd of less than $10^{-6}$ M. While it may be preferred to employ alpha-helices comprising 3-5 amino acid repeats of an amino acid motif (of e.g. 4-9 amino acid residues, i.e. 4-mers to 9-mers), a higher number of repeats is feasible using a shorter amino acid motif (e.g. 3-mers to 6-mers), and a lower number of repeats is feasible using a longer amino acid motif (e.g. 7-mers to 10-mers).

Specifically, said anti-CD32 moiety is selected from the group consisting of an anti-CD32 antibody, an antibody fragment and a peptide, preferably targeting CD32a.

Specifically, said TLR9 ligand is a TLR9 agonist selected from the group consisting of CpG oligodeoxynucleotides class A, B and C, or an immunostimulatory peptide mimicking any of the CpG oligodeoxynucleotides.

Specifically, the immunogenic composition comprises one or more linker sequences, specifically flexible linker, preferably composed of glycine and/or serine and/or lysine residues, preferably an amino acid sequence SEQ ID 4 or 5.

Specifically, component b. of the immunogenic composition comprises or consists of the amino acid sequence SEQ ID 9 or SEQ ID 10.

Specifically, component a. (directed adjuvant) of the immunogenic composition comprises the amino acid sequence SEQ ID 3.

The invention further provides a vaccine comprising the immunogenic composition of the invention, and a pharmaceutically acceptable carrier. Such vaccine is typically an immunostimulating vaccine, e.g. stimulating the humoral and T-cell (Th1) immune response.

According to a preferred embodiment, the humoral and T-cell (Th1) immune response is transient, e.g. with a specific maximum IgG titer induced upon vaccination that is typically achieved within a period of 2 to 8 weeks upon vaccination, followed by a titer reduction by at least 30%, preferably at least 40%, or at least 50%, or at least 60%, or at least 70%, or at least 80%, or at least 90%, or up to 100%, within 6 months upon vaccination, preferably within 5 months, or within 4 months, or within 3 months, or within 2 months. Such reduced titer may be again increased upon a booster injection. In a series of vaccination, the transient immune response is possibly determined upon the last injection of the immunogenic composition or vaccine. The transient immune response has the advantage of a controlled treatment with, e.g. the possibility to interrupt or stop treatment as necessary.

The invention further provides a kit for preparing the immunogenic composition of the invention, comprising the following components
   a. a directed adjuvant comprising at least an anti-CD32 moiety linked to a TLR9 ligand and a first peptidic alpha-helix; and
   b. an immunogen comprising an extracellular Her2/neu domain that is linked to a second peptidic alpha-helix coiled to the first alpha-helix.

The kit may specifically be used to facilitate the production of the vaccine by using the preformed directed adjuvant component for the combination with an immunogen that may be provided according to the need of a subject group or the individual subject.

According to a specific aspect, the immunogenic composition of the invention is provided for medical use. In particular, the immunogenic composition is provided for use in treating a subject suffering from Her2/neu positive tumor diseases, such as breast, ovarian, stomach, uterine, colorectal and non-small cell lung cancer. Such disease or disease condition is primarily caused by or associated with the endogenous Her2/neu overexpression produced by tumor cells.

Thus, the invention specifically provides for a method of treating a subject suffering from Her2/neu positive tumor diseases, by administering to the subject an effective amount of the immunogenic composition or the vaccine of the invention, either prophylactically, e.g. to prevent the outbreak of a disease or disease condition or the progress of disease, or therapeutically, e.g. to ameliorate a disease or disease condition.

Specifically, the immunogenic composition is administered to the subject in an effective amount employing a prime-boost strategy.

Specifically, the composition is administered to the subject in an effective amount ranging between 0.0001 and 2 mg per administration, preferably between 0.001 and 2 mg per dose.

Specifically, the subject is further treated by chemotherapy, immunotherapy, inhibitor therapy and/or radiotherapy, e.g. in the course of treating a Her2/neu positive cancer.

According to a specific aspect, the subject is further treated by passive immunotherapy including but not restricted to monoclonal or polyclonal antibody inhibitors of PD1 and CTL4, or their ligands or receptors.

According to a further specific aspect, the subject is further treated by checkpoint kinase 1 and/or checkpoint kinase 2 inhibitors such as AZD7762 or PF-477736.

Accordingly, cancer patients may have stopped other cancer treatment or they may start additional other cancer treatments during treatment with the vaccine or they may still be treated with other cancer treatment while starting treatment with the present immunogenic composition or vaccine.

Specifically, the immunogenic composition triggers a protective immune response in the subject, preferably with a serum IgG titer against Her2/neu of at least 1/100, preferably at least $1/10^4$, preferably at least $1/10^5$, preferably at least $1/10^6$, or lower, thus, detectable at a higher dilution.

When more than one Her2/neu domains are bound to the second alpha-helix, specifically wherein each of the Her2/neu domains is linked by covalent binding or fusion (avoiding agglomeration or oligomerization of otherwise unbound or free Her2/neu domains), the Her2/neu domains may e.g. be conjugated to the alpha-helix consecutively, i.e. linking the Her2/neu domains in a row, e.g. linking the C-terminus of a first Her2/neu domain to an N-terminus of a second Her2/neu domain, which first and second Her2/neu domains are identical or differ from each other.

Alternatively, or in addition, further Her2/neu domains may be incorporated into the immunogenic composition of the invention by cross-linking e.g. two or more Her2/neu domains, which are either identical or differ from each other, are linked to the same alpha-helix by chemical reaction, such as chemical cross-linking permitting the establishment of inter-molecular cross-linkages, e.g. with homo-bifunctional reagents such as Dimethyl adipimidate (DMA), Dimethyl suberimidate (DMS), or glutaraldehyde. For example, such cross-linking may be performed employing glutaraldehyde crosslinking by free lysine groups of the alpha-helix or a spacer/linker, respectively. Thereby, two or more Her2/neu domains as used according to the invention are coupled to the alpha-helix in parallel, or side-by-side.

According to a specific aspect of the invention, each of said first and second alpha-helices comprises 2-9 amino acid repeats of an amino acid motif, specifically 3-7, or 3-6, or 3-5 amino acid repeats, wherein the alpha-helices specifically bind to each other with a Kd of less than $10^{-6}$ M, preferably with a Kd of less than $10^{-7}$ M, more preferred less than $10^{-8}$ M or $10^{-9}$ M.

According to a further specific aspect of the invention, said anti-CD32 moiety is selected from the group consisting of an anti-CD32 antibody, an antibody fragment and a peptide, preferably targeting CD32a. The antibody fragment specifically may e.g. be an Fab, Fv, scFv, dAb, F(ab)2 or Fcab fragment, or any other possible binding entity, as long as it specifically binds to the receptor and is internalized after binding.

Specifically said anti-CD32 moiety is targeting CD32a, preferably with a high affinity of Kd≤$10^{-6}$ M, more preferred less than $10^{-7}$ M or less than $10^{-8}$ M.

More specifically said anti-CD32 moiety is a specific or selective CD32a binder, i.e. not targeting CD32b or targeting CD32b with a low affinity of Kd>$10^{-6}$ M, preferably higher than $10^{-5}$ M, more preferred higher than $10^{-4}$ M. The differential affinity of binding to CD32a and CD32b is preferably at least 1 log, more preferred at least 2 logs or at least 3 logs of higher difference in the Kd value.

The specifically preferred high affinity or high differential affinity of the anti-CD32 moiety to bind CD32a rather than CD32b is typically used in an immunostimulating vaccine further employing the agonistic TLR9 ligand.

Binding affinity of the anti-CD32 moiety targeting specifically any of CD32a or CD32b, or both, CD32a and CD32b, can be determined in a suitable assay such as a typical ELISA using commercially available HIS-tagged recombinant forms of CD32a and CD32b, coated to Ni-NTA ELISA plates, e.g. Ni-NTA HisSorb Plates (Qiagen, Austria). The anti-CD32 moieties may be biotinylated and as such may be detected using streptavidine-HRP or streptavidine AP and the appropriate substrates. Alternatively the moieties may be tested in a FACS assay using U937 cells (e.g. ATCC: CRL 1593) expressing CD32a but not CD32b and EBV transformed B cells e.g. CFB4:2 as described by van Reijsen et al.[14], expressing CD32b and not CD32a According to a further specific aspect of the invention, said TLR9 ligand is a TLR9 agonist selected from the group consisting of CpG oligodeoxynucleotides class A, B and C, or an immunostimulatory peptide mimicking any of the CpG oligodeoxynucleotides.

According to a specific aspect of the invention, the TLR9 ligand is a TLR9 agonist selected from the group consisting of CpG class A, in particular CpG-A (D)[11] oligodeoxynucleotides (ODN), also known as "D"-type ODN. Such TLR9 agonists induce a strong IFNa induction and minimal maturation of dendritic cells, and are herein called "group 1" TLR9 ligand.

According to another specific aspect of the invention, the TLR9 ligand is a TLR9 agonist selected from the group consisting of CpG class B, in particular CpG-B (K)[15] oligodeoxynucleotides (ODN), also known as "K"-type ODN. Such TLR9 agonists induce a weak IFNa induction and maturation of dendritic cells, and are herein called "group 2" TLR9 ligand.

According to another specific aspect of the invention, the TLR9 ligand specifically is a TLR9 agonist selected from the group consisting of CpG class C, also known as CpG-C[9;15] oligodeoxynucleotides (ODN). Such TLR9 agonists induce IFNa and maturation of immature dendritic cells, and are herein called "group 3" TLR9 ligand.

The induction of IFNa may be determined by the level of IFNa expression and the respective increase with respect to a reference level. The increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

The maturation of immature dendritic cells may be determined by the level of expression of any of the markers CD80, CD83 and CD86. The respective increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

Specifically, the TLR9 agonist of group 1 and 3 would result in an increased IFNa expression and a TRL9 agonist of group 2 and 3 would lead to an increased expression of any of the DC maturation factors CD80, CD83 and CD86. The TLR9 antagonist would result in a reduced IFNa expression and a reduced expression of any of the DC maturation factors CD80, CD83 and CD86, even in the presence of a TLR9 agonist of either group 1-3.

As an alternative to the polynucleotide TLR9 ligands as described above, any other TLR9 binder with agonistic effect may be used, e.g. a peptide binder or protein binder, including antibodies or antibody fragments.

According to a further specific aspect of the invention, the immunogenic composition comprises one or more linker sequences, preferably composed of glycine and/or serine and/or lysine residues, preferably an amino acid sequence SEQ ID 4 or 5. The linker sequences may be linear or branched, e.g. to provide linkage or cross-linkage between two or more peptide or polypeptide entities.

FIGURES

FIG. 1 shows representative example of 3 animals. After immunization with OQR200 (stars) on d1, d15 and d36 IgG anti Her2 antibodies (closed triangles) can be detected. First antibodies against Her2 can be detected before $2^{nd}$ immunization on d15. Peak antibody titers are seen 2 weeks after $2^{nd}$ and $3^{rd}$ immunization after which titers start to decline until next boost (d36 and d127), which induces a new strong increase in antibody titer. Indicating reversibility of the treatment and the absence of treatment induced autoimmune disease.

Figure 2:
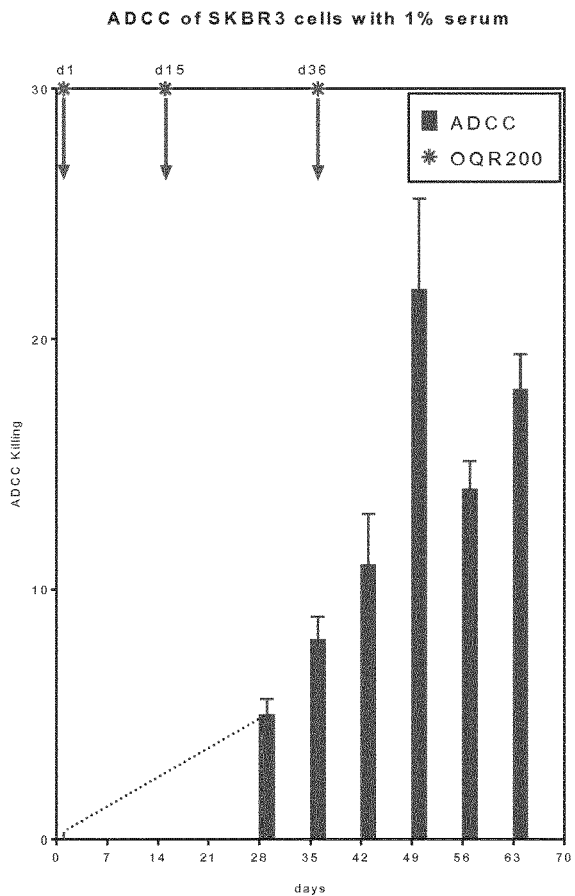
Figure 3:
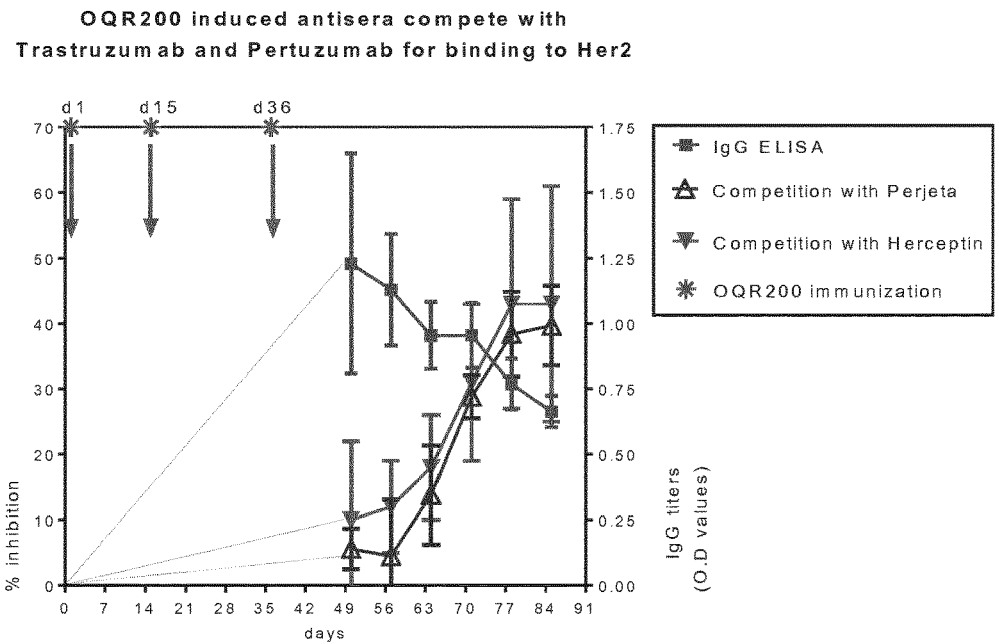

FIG. 2 shows antibody-dependent cellular cytotoxicity (ADCC). Serum from d28, d35, d42, d49, d63 and d70 were tested 1/100 diluted for the capacity to kill Her2 expressing SKBR3 cells. Maximum killing was seen 2 weeks after $3^{rd}$ immunization, at the top of the IgG time curve (FIG. 1). Killing at d63 was stronger than at d56 despite that total IgG against Her2 was lower at that day (FIG. 1) indicating that the quality of the anti Her2 antibodies has improved due to affinity maturation FIG. 3 shows epitope mapping using Trastuzumab and Pertuzumab. Animals were immunized with OQR200 on d1, d15, and d35. Sera taken between d50 and d88 were tested for their ability to block binding of Trastuzumab (closed triangles, left Y-axis) and Pertuzumab (open triangles, left Y-axis) to human Her2 in ELISA. Despite decreasing anti Her2 IgG titers between d50 and d88 (blocks, right Y-axis) both Trastuzumab and Pertuzumab were more efficiently prevented to bind to their respective epitopes with sera taken at later time points after immunization. Optimal blocking was seen between d77 and d85, this shows that the quality of the anti Her2 antiserum increases over time by means of affinity maturation.

Figure 4:
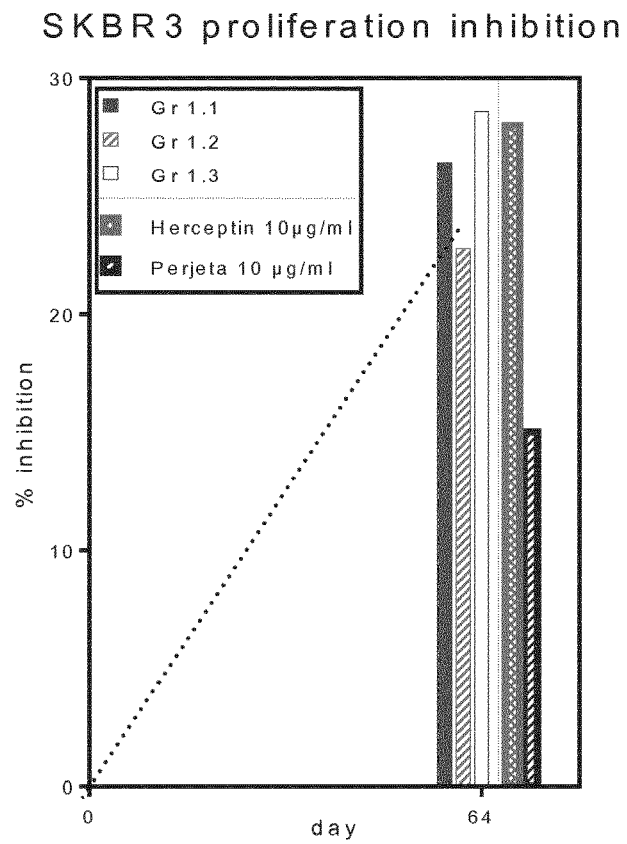

FIG. 4 shows proliferation inhibition. Animals were immunized with OQR200 on d1, d15, and d35. Sera taken at day 64 were tested for their ability to inhibit proliferation of a Her/neu expressing breast cancer cell line (SKBR3) (closed, hatched and open bar with thin borders) and compared to clinically effective block buster antibodies Trastuzumab (Herceptin; crossed bar and thick border)) and Pertuzumab (Perjeta; hatched bar thick border). Monkey sera were comparable to Herceptin and better than Perjeta in inhibiting SKBR3 proliferation.

FIG. 5 shows sequence information of materials referred to herein.

SEQ ID 1: Amino acid-Sequence CyErb2 (Her2/neu from Cynomolgus monkeys)
SEQ ID 2: Amino acid-Sequence Erb2 (Her2/neu from humans)
SEQ ID 3: Amino acid sequence of ScFV-coil1
SEQ ID 4: Amino acid sequence of linker between Her2 and pepK containing HIS tag
SEQ ID 5: Amino acid sequence of linker between Her2 and pepK
SEQ ID 6: Nucleotide sequence of TRL9 agonist CpG class A: ODN2216
SEQ ID 7: Nucleotide sequence of TRL9 agonist CpG class B: ODN2006
SEQ ID 8: Nucleotide sequence of TRL9 agonist CpG class C: ODNM362
SEQ ID 9: Amino acid-Sequence CyErb2-coil (Her2/neu from Cynomolgus monkeys including pepK of the S-TIR technology)
SEQ ID 10: Amino acid-Sequence Erb2-coil (Her2/neu from humans including pepK of the S-TIR technology), including a linker and a HIS tag.
SEQ ID 38: Amino acid-Sequence Erb2-coil (Her2/neu from humans including pepK of the S-TIR technology), including a linker

DETAILED DESCRIPTION OF THE INVENTION

Specific terms as used throughout the specification have the following meaning.

The term "adjuvant" as used herein shall mean an integrated or co-administered component of a vaccine, which:
  enhances the immune response to a specific immunogen, e.g. an antigen or a hapten. The immune response is typically greater than the immune response elicited by an equivalent amount of the immunogenic composition administered without the adjuvant,
  and/or
  the adjuvant is used to direct a particular type or class of immune response against the immunogen, e.g. a Th1 or Treg type of immune response, herein understood as "directed adjuvant".

An "effective amount" of an adjuvant of the present invention specifically is an amount which enhances an immunological response to the immunogen such that, for example, lower or fewer doses of the immunogenic composition are required to generate an efficient immune response of the intended class.

The directed adjuvant according to the invention not only mediates the efficient immune response, but also the regulation of the immune response in the desired way. By directing the immunogen to the appropriate immune cells for its internalization and further processing, the Th1 immune response is induced rather than the Th2 immune response, in particular when employing a TLR9 ligand that is a TLR9 agonist of group 3. If a TLR9 agonist of group 1 is combined with an anti-CD32 moiety that binds CD32b, the induction of Treg cells is usually anticipated.

An "effective amount" of an immunogenic composition, e.g. as used in a vaccine of the invention refers to an amount sufficient to show a meaningful benefit in a subject being treated, when administered as part of a vaccination dosing regimen. Those of ordinary skill in the art will appreciate that, in some embodiments, a particular composition may be considered to contain a prophylactically or therapeutically effective amount if it contains an amount appropriate for a unit dosage form administered in a specific dosing regimen, even though such amount may be insufficient to achieve the meaningful benefit if administered as a single unit dose. Those of ordinary skill will further appreciate that an effective amount of an immunogenic composition may differ for different subjects receiving the composition, for example depending on such factors as the desired biological endpoint, the nature of the composition, the route of administration, the health, size and/or age of the subject being treated, etc. In some embodiments, an effective amount is one that has been correlated with beneficial effect when administered as part of a particular dosing regimen, e.g. a single administration or a series of administrations such as in a "boosting" regimen.

The term "peptidic alpha-helix" as used herein shall mean a coiled structural motif based on a peptide sequence comprising a number of repeats, also called coil repeats. Such alpha-helix is capable of binding to another counterpart, also called matching alpha-helix of the same type to form a dimer, trimer or further oligomer, also called coiled coil.

A coiled coil is a structural motif in polypeptides or peptides, in which two to seven alpha-helices are coiled together like the strands of a rope. In some embodiments, the coiled coil of the vaccine is one with two alpha-helices coiled together. Such alpha helical regions are likely to form coiled-coil structures and may be involved in oligomerization of the coil repeats as measured in a suitable coiled coil interaction binding assay.

Specifically a dimer of alpha-helices can be formed by contacting the two monomers, such that the dimer is formed through an interaction with the two alpha helix coiled coil domains. In some embodiments the coils comprise a peptide with the amino acid sequence as set forth in SEQ ID NO: 11 or 12 (coil and anti-coil), which include x repeats.

(SEQ ID 11)
EVSAL

E5:
(SEQ ID 13)
EVSALEKEVSALEKEVSALEKEVSALEKEVSALEK-NH2

(SEQ ID 12)
KVSAL

K5:
(SEQ ID 14)
KVSALKEKVSALKEKVSALKEKVSALKEKVSALKE-NH2

Alternatively, any of the sequences described by Chao et al.[16] or Litowsky et al.[17;18] or functional equivalents, which generate the specific coiled-coil type linkage, may be used, such as indicated in the following table, including variants thereof, e.g. with a different number of repeats, or one, two or three point mutations in the coil type:

| Coil Type | Type/number of repeats: Exemplary sequence |
|---|---|
| EIAAL (SEQ ID 15) | E3: EIAALEKEIAALEKEIAALEK-NH2 (SEQ ID 21) |
| EIAAL (SEQ ID 15) | E4: EIAALEKEIAALEKEIAALEKEIAALEK-NH2 (SEQ ID 22) |
| KIAAL (SEQ ID 16) | K3: KIAALKEKIAALKEKIAALKE-NH2 (SEQ ID 23) |
| KIAAL (SEQ ID 16) | K4: KIAALKEKIAALKEKIAALKEKIAALKE-NH2 (SEQ ID 24) |
| EISAL (SEQ ID 17) | E3: EISALEKEISALEKEISALEK-NH2 (SEQ ID 25) |
| EISAL (SEQ ID 17) | E4: EISALEKEISALEKEISALEKEISALEK-NH2 (SEQ ID 26) |
| KISAL (SEQ ID 18) | K3: KISALKEKISALKEKISALKE-NH2 (SEQ ID 27) |
| KISAL (SEQ ID 18) | K4: KISALKEKISALKEKISALKEKISALKE-NH2 (SEQ ID 28) |
| EVAAL (SEQ ID 19) | E3: EVAALEKEVAALEKEVAALEK-NH2 (SEQ ID 29) |
| EVAAL (SEQ ID 19) | E4: EVAALEKEVAALEKEVAALEKEVAALEK-NH2 (SEQ ID 30) |
| KVAAL (SEQ ID 20) | K3: KVAALKEKVAALKEKVAALKE-NH2 (SEQ ID 31) |
| KVAAL (SEQ ID 20) | K4: KVAALKEKVAALKEKVAALKEKVAALKE-NH2 (SEQ ID 32) |
| EVSAL (SEQ ID 11) | E3: EVSALEKEVSALEKEVSALEK-NH2 (SEQ ID 33) |
| EVSAL (SEQ ID 11) | E4: EVSALEKEVSALEKEVSALEKEVSALEK-NH2 (SEQ ID 34) |
| KVSAL (SEQ ID 12) | K3: KVSALKEKVSALKEKVSALKE-NH2 (SEQ ID 35) |
| KVSAL (SEQ ID 12) | K4: KVSALKEKVSALKEKVSALKEKVSALKE-NH2 (SEQ ID 36) |

For the purpose of the invention, the preferred type of a coiled coil is a dimer, either a heterodimer (heterocoil) of two different, but matching helices, which differ in at least one amino acid in the coil repeat sequence, or else a homodimer of two identical matching helices, i.e. those comprising the matching coil repeat sequences (the "coils").

Specifically, the number of coil repeats is 2-9, specifically 3-5, preferably any of the combinations 3+3, 3+4, 3+5, 4+4, 4+5, 5+5, 4+3, 5+3 or 5+4.

As an alternative to heptad repeats (repeats of an amino acid sequence consisting of 7 amino acids, 7-mers), 3-mers, 4-mers, 5-mers, 6-mers, 8-mers, 9-mers, or 10-mers may be used.

In case of a homodimeric coiled coil, the typical number of coil repeats is specifically not more than 5, so to avoid undesired mismatches of the structure. In case of a heterodimeric coiled coil, it is typically desirable to employ a length of the peptide sequence with at least 3 coils. Thereby the binding of the components of the vaccine, i.e. the directed adjuvant and the immunogen components, to each other is typically achieved with preferred high affinity of a Kd of less than $10^{-7}$ M, more preferred less than $10^{-8}$ M or $10^{-9}$ M. However, although more repeats increase the affinity, this may be at the cost of increased homodimerisation.

The components of the immunogenic composition of the invention may also comprise a peptide spacer so to link the anti-CD32 moiety and/or the TLR9 ligand, and optionally also the epitopes (of the Her2/neu domain) with the coil repeats, respectively. For example, the peptide spacer can be on either or both ends of a coiled coil. Each of the peptide spacers can be attached to a single alpha helix coiled coil domain of the coiled coil.

The peptide spacer can be, for example, a peptide of 5, 6, 7, 8, 9, 10, 15, 20, 25, 30, 35, 40, 45 or 50 amino acids or more, either linear or branched, e.g. to provide for two, three, four, or more branches. The number of amino acids in the peptide spacer may be, in some embodiments, 20 amino acids or up to 10 amino acids greater or fewer, depending on the particular sequences and length of the coil.

The term "anti-CD32 moiety" as used herein shall mean a ligand specifically binding to the cellular target CD32, either CD32a, CD32b or both, CD32a and CD32b. The moiety can be any binding structure, such as derived from proteins, polypeptides or peptides, including antibodies and antibody fragments or composite molecules with a binding part. The binding part of the molecules or molecule complex of the invention can be comprised of proteins such as antibodies or antibody fragments, such as Fab, Fv, scFv, dAb, F(ab)2, minibody, small mutated immunoglobulin domains, or other biological binders, such as soluble T-cell receptor, Darpins, etc. Antibodies and antibody fragments and derivatives may be generated and selected for binding to CD32 according to known methods such as hybridoma technology, B-cell cloning, phage display, ribosome display or cell surface display of antibody libraries, array screening of variant antibodies. Exemplary anti-CD32 moieties are scFv derived from the anti CD32 monoclonal antibody AT-10[19], IV.3[20], 2E1[21] or any other aCD32 monoclonal antibody.

The specific binding may be determined in a suitable binding assay, such as conventional immunoassays. There are numerous methods known in the art for detecting binding in an immunoassay. Various immunoassays known in the art can be used including competitive and non-competitive assay systems using techniques such as radioimmunoassays, ELISA (enzyme linked immunosorbent assay), immunoradiometric assays, gel diffusion precipitation reactions, immunodiffusion assays, western blot, BIAcore etc.

The term "cross-reactive" with respect to antigens or antibodies as used herein shall refer to epitopes shared between antigens of different origin, e.g. from human, rhesus monkey or mouse origin. The N-terminal epitope consisting or comprising the first 4 AA of G17 was found to be cross-reactive in peptides of various origin, which epitope triggers an immune response and IgG antibodies that are cross-reactive with the epitopes.

The immunogenic composition of the invention is specifically useful to treat Her2/neu positive tumor diseases or disease conditions in which Her2/neu overexpression is playing a role.

The term "Her2/neu positive tumor" as used herein shall refer to tumors or disease or disease conditions associated therewith, of e.g. breast, ovarian, stomach, uterine, colorectal and non-small cell lung cancer. The term is specifically used herein with regard to treating the tumor for preventing tumor disease progression, for a positive tumor response or for tumor shrinkage. The term is also applied to minimal residual disease, which would be successfully treated, e.g. targeting circulating tumor cells to reduce their number below a certain threshold, e.g. below the detection limit.

The term "Her2/neu domain" or "Extracellular Her2/neu domain" as used herein shall refer to the Her2/neu protein including the extracellular domain of Her2/neu, or at least part of it. Specifically, the Her2/neu domain may or may not comprise the intracellular domain, and optionally comprises at least the T-cell epitopes of the intracellular domain. Preferably, the Her2/neu domain does not comprise the transmembrane domain.

The Her2/neu domain may be of human origin, or other mammalian origin, including rhesus monkey, or mouse, thus, has a human or other mammalian sequence, or may be an artificial construct, such as to incorporate artificial sequences, e.g. obtained by changing the type and/or sequence of amino acid residues in the native (naturally occurring) sequence. The term shall specifically include variants of human Her2/neu domain, with an amino acid sequence SEQ ID 1 or SEQ ID 2, or sequences with a certain sequence identity thereto, or fragments thereof, e.g. a fragment or hybrid polypeptide combining or fusing at least two fragments of the Her2/neu domain (to obtain a hybrid), but differs from its amino acid sequence, in that it is derived from a homologous sequence of a different species. These are referred to as naturally occurring variants or analogs. The term "analogs" shall also refer to chimeric constructs originating from two or more origins, wherein at least one part is naturally-occurring, e.g. which constitutes the major part (at least 50%) of the Her2/neu domain, and another part is different thereto, either naturally occurring or non-naturally occurring (synthetic or artificial).

The term shall specifically include fragments or functionally active variants of the Her2/neu domain, e.g. those comprising one or more point mutations, or else peptides or polypeptides comprising further amino acid sequences besides the Her2/neu domain, e.g. by extending the N-terminus and/or the C-terminus by additional one or more amino acid residues or sequences. An extension of the C-terminus is e.g. preferred with repeats of Her2/neu domain sequences, either identical or not, or with further amino acid sequences of the Her2/neu protein.

The term "functionally active variants" as used herein with respect to the Her2/neu domain as described herein, shall mean a sequence resulting from modification of this sequence (a parent sequence), e.g. by insertion, deletion or substitution of one or more amino acids, such as by recombination techniques or chemical derivatization of one or more amino acid residues in the amino acid sequence, or nucleotides within the coding nucleotide sequence, or at either or both of the distal ends of the sequence, and which modification does not affect (in particular impair) the activity of this sequence. In the case of a Her2/neu domain eliciting a certain immune response to target Her2/neu, the functionally active variant of the Her2/neu domain would still incorporate the antigenic determinant or epitope, though this could be changed, e.g. to increase the immunogenicity. Specifically, the functionally active variants of the Her2/neu domain have the potency to elicit IgG anti-gastrin antibodies in a treated subject, which antibodies cross-react with the endogenous Her2/neu receptor on the surface of tumor cells. Functionally active variants can further be characterized by eliciting the desired T-cell immune response. Including CD4+ Th cells and/or CD8+ Tc cell which may be directed against any part of the Her2/neu protein either the intracellular or the extra cellular domain thus providing the necessary T cell help for antibody production of activation of the CD8 cells which may directly kill the Her2/neu expressing tumor cell Functionally active variants may be obtained, e.g. by changing the sequence of a parent Her2/neu domain, e.g. the human, rhesus monkey or murine Her2/neu domain, or a fragment thereof, by introducing one or more modifications that do not substantially impair the epitopes, to obtain a molecule with substantially the same immunogenicity. The term "substantially the same immunogenicity" as used herein refers to the amount of an immune response or anti-Her2/neu IgG antibodies induced in a subject treated with the immunogenic composition, which amount is preferably at least 20% at least 30% at least 40%, at least 50% at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the amount as determined for the parent polypeptide.

In a preferred embodiment the functionally active variant of a parent polypeptide a) is derived from the polypeptide by at least one amino acid substitution, insertion (addition) and/or deletion, e.g. comprising one or more point mutations wherein the functionally active variant has a specific sequence identity to the parent molecule, such as at least 50% sequence identity, preferably at least 60%, more preferably at least 70%, more preferably at least 80%, still more preferably at least 90%; and/or b) consists of the polypeptide and additionally at least one amino acid heterologous to the polypeptide.

Functionally active variants may be obtained by sequence alterations in the polypeptide sequence, e.g. by one or more point mutations, wherein the sequence alterations substantially retains a function of the unaltered polypeptide sequence, when used in according to the invention. Such sequence alterations or point mutations can include, but are not limited to, (conservative) substitutions, additions, deletions, mutations and insertions, e.g. the alteration of 1, 2, 3, or 4 amino acids, or by addition or insertion of one to several amino acids, e.g. 1, 2, 3, or 4 amino acids, or by a chemical derivatization of one to several amino acids, e.g. 1, 2, 3, or 4, or combination thereof, preferably by point mutations that are not contiguous. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

Preferred point mutations refer to the exchange of amino acids of the same polarity and/or charge. In this regard, amino acids refer to twenty naturally-occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the polypeptide sequences described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

Functionally active variants may be obtained by any of the known mutagenesis methods, including point mutations at desired positions, e.g. obtained by randomisation techniques. In some cases positions are chosen randomly, e.g. with either any of the possible amino acids or a selection of preferred amino acids to randomise the polypeptide sequences. In this regard, the term "mutagenesis" refers to any art recognized technique for altering a polynucleotide or polypeptide sequence.

The term "immunogen" as used herein shall mean an antigen or immunogen of polypeptide or peptidic structure, in particular an immunogen that comprises or consists of a polypeptide or peptide of a specific amino acid sequence, which is either provided as a linear polypeptide (peptide) or branched polypeptide (e.g. a synthetic polypeptide or peptide), comprising naturally occurring amino acid residues or modified ones, e.g. a derivative obtained by modification or chemical derivatization, such as by phosphorylation, methylation, acetylation, amidation, formation of pyrrolidone carboxylic acid, isomerization, hydroxylation, sulfation, flavin-binding, cysteine oxidation and nitrosylation.

The immunogen or Her2/neu domain as used herein is specifically designed to trigger an immune response in a subject, and particularly includes one or more antigenic determinants, which can be possibly recognized by a binding site of an antibody or is able to bind to the peptide groove of HLA class I or class II molecules or other antigen presenting molecules such as CD1 and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope, which are immunologically relevant, i.e. are also recognizable by natural or monoclonal antibodies. Herein the use of B cell epitopes and T cell epitopes is specifically preferred.

The term "epitope" as used herein according to the present invention shall in particular refer to a molecular structure which may completely make up a specific binding partner or be part of a specific binding partner to a binding site of an antibody. Chemically, an epitope of a Her2/neu domain of the present invention may be a peptide epitope that usually includes at least 3 amino acid residues, preferably 4, 5, 6, 7, 8, 9, 10, 11, 12 or 13 amino acids. There is no critical upper limit to the length of the peptide, which could comprise even the full length of an amino acid sequence of a protein.

The Her2/neu domain of the invention is specifically understood as a self-antigen. The term "self-antigen" as used herein means any antigen, specifically polypeptide or peptide produced by a normal, healthy subject that does not elicit an immune response as such. These self-antigens may be produced at aberrant or high levels in certain disease states, including cancer disease, so called tumour associated antigens (TAAs). Herein, the Her2/neu is understood as a self-antigen in human subjects, and specifically as a TAA in subjects suffering from a Her2/neu positive (or overexpressing) tumor.

It is understood that the self-antigens such as used according to the invention, can be naturally-occurring, recombinantly or synthetically produced. It is also understood that the self-antigens need not be identical to the naturally produced antigen, but rather can include variations thereto having certain sequence identities, similarities or homology.

The Her2/neu domain or the immunogenic composition used in the vaccine as described herein, is usually contained in a vaccine in an effective amount, which is herein specifically understood as "immunologically effective amount". By "immunologically effective amount", it is meant that the administration of that amount to a subject, either in a single dose or as part of a series of doses, is effective on the basis of the therapeutic or prophylactic objectives. This amount will vary depending upon the health and physical condition of the subject to be treated, age, the capacity of the subject's immune system to synthesize antibodies, the degree of immune response desired, the formulation of the vaccine, and other conditions.

The invention also provides a method for treating a subject or raising an immune response in a subject, comprising the step of administering an immunologically effective amount of the peptide immunogen, the immunogenic composition or the vaccine of the invention.

An effective amount or dosage may range from 0.0001 to 2 mg, e.g. between 0.001 and 2 mg, of the immunogenic composition administered to the subject in need thereof, e.g. an adult human subject. The effective dosage of the immunogenic composition is capable of eliciting an immune response in a patient of effective levels of antibody titer to bind to endogenous Her2/neu, e.g. 1-3 months after immunization. The effectiveness of the therapy may be assayed by the Her2/neu antibody titers in samples of blood taken from the subject, or by measuring tumor load using classical clinical methods to monitor the presence of absence of individual tumors.

The term "TLR9 ligand" as used herein is understood in the following way.

Toll-like receptor 9 (TLR9) recognizes unmethylated bacterial CpG DNA and initiates a signalling cascade leading to the production of proinflammatory cytokines. There are numerous structures or sequences that have been shown to act as a ligand of TLR9, i.e. bind to this receptor and thereby either activate (stimulate, upregulate, TLR9 agonist) or de-activate (downregulate, TLR) antagonist) TLR9. For instance, microbial DNA or synthetic DNA, e.g. synthetic CpG ODN may stimulate TLR9 with variations in the number and location of CpG dimers, as well as the precise base sequences flanking the CpG dimers. Synthetic CpG ODN differ from microbial DNA in that they have a partially or completely phosphorothioated backbone instead of the typical phosphodiester backbone and may or may not have a poly G tail at the 3' end, 5' end, or both.

The term "agonist" in conjunction with the TLR9 ligand as used herein shall specifically refer to the binding and activation of TLR9 in a cell-based assay.

The TLR9 ligand which is composed of a nucleotide sequence is typically coupled to the directed adjuvant component of the present immunogenic composition by chemical coupling e.g. using the commercially available Kit from Solulink. A peptidic TLR9 ligand may be coupled using standard peptide chemistry or may be integrated using recombinant DNA technology.

Exemplary TLR9 ligands are ODN 2216[22] (group 1), ODN 2006/ODN 2007[15] (group2) and CpG-M362[13] (group 3).

Further exemplary TLR9 ligands may be peptides that mimic the action of a CpG TLR9 agonist, e.g. identified by or obtained from a peptide library, which are selected for the affinity to bind the TLR9 and proven agonistic activity, or protein ligands, including specific antibodies.

The function of a TLR9 ligand or agonist may be determined in a suitable assay, e.g. in the following way: pDCs are purified from blood of a healthy donor as described by Tel et al.[23] and subsequently incubated with the appropriate concentration of the TLR9 ligand. After 24 h IFNa is measured in the supernatant using standard ELISA protocols. For determination of the maturation state of the cells, pDCs are stained for expression of CD80 CD83 or CD86 using standard FACS procedures with commercially available specific antibodies before and after the incubation with the TLR9 ligand.

The number of reactive T cells that are activated upon exposure to the vaccine according to the invention may be determined by a number of methods including ELISPOT, FACS analysis, cytokine release, or T cell proliferation assays.

As used herein, the term "specificity" or "specific binding" refers to a binding reaction which is determinative of the cognate ligand of interest in a heterogeneous population of molecules. Thus, under designated conditions (e.g. immunoassay conditions), one or more antigens are specifically bound by the respective binding site(s) of a binder, which does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "treatment" as used herein shall always refer to treating subjects for prophylactic (i.e. to prevent infection and/or disease status) or therapeutic (i.e. to treat diseases regardless of their pathogenesis) purposes. Treatment of a subject will typically be therapeutic in cases of cancer disease conditions, including Her2/neu positive tumors or Her2/neu overexpressing cancer. However, in case of patients suffering from a primary disease, which are at risk of disease progression or at risk of developing a secondary disease condition or side reaction, the treatment may be prophylactic.

Treatment may be effected with the immunogenic composition or the vaccine as described herein, as the sole prophylactic or therapeutic agent or else in combination with any suitable means, e.g. including chemotherapy, radiotherapy or immunotherapy, such as passive antibody treatment against the tumor itself or indirectly against immune suppressive mechanism targeting PD-1 and/or CTLA4, as well as enzyme inhibitor therapy, e.g. checkpoint inhibitors such as AZD7762 or PF-477736.

In cancer therapy, additional therapeutic treatments include, for instance, surgical resection, radiation therapy, chemotherapy, hormone therapy, anti-tumor vaccines, antibody based therapies, whole body irradiation, bone marrow transplantation, peripheral blood stem cell transplantation, and the administration of chemotherapeutic agents.

The term "combination" as used in this regard, e.g. with respect to the combination of compounds or treatments specifically refers to the concomitant, simultaneous, parallel or consecutive treatment of a subject.

For treatment the immunogenic composition or the vaccine as described herein may be administered at once, or may be divided into the individual components and/or a number of smaller doses to be administered at intervals of time. The vaccine is typically administered at a concentration of 0.1 to 500 μg/mL, e.g. either subcutaneously, intradermally, intramuscularly, intravenous, orally, through inhalation or intranasally, with or without an additional adjuvant such as ALUM. It is understood that the precise dosage and duration of treatment is a function of the disease being treated and may be determined empirically using known testing protocols or by extrapolation from in vivo or in vitro test data.

The immunogenic composition or the vaccine as described herein can be administered by any suitable means and respective formulations for including, but not limited to, for example, any of the parenteral (including subcutaneous, intramuscular, intravenous and intradermal) injection, or local injection into the affected site, such as joints or into or around the tumor. In a preferred embodiment the vaccine is provided in a formulation for intramuscular, subcutaneous or intradermal injection.

The invention also provides a delivery device, e.g. a syringe, pre-filled with the vaccine as described herein.

Typically upon priming a subject by a first injection of a vaccine according to the invention, one or more booster injections may be performed over a period of time by the same or different administration routes. Where multiple injections are used, subsequent injections may be made, e.g. within 1 to 52 weeks of the previous injection, or even more.

The vaccine typically may contain diluents, such as water, saline, glycerol, ethanol, etc. Additionally, as auxiliary substances, such as wetting or emulsifying agents, pH buffering substances, and the like, may be present among excipients. Typically, the vaccine according to the invention is prepared as an injectable, either as liquid solutions or suspensions, or solid forms suitable for solution in, or suspension in, liquid vehicles prior to administration. The preparations also may be emulsified or encapsulated in liposomes.

Administration of the vaccine as described herein may be suitably and additionally be combined with any of the TLR9 agonists and/or further adjuvant measures, e.g. as separate entities in the same formulation or as separate formulations, to enhance the immune response.

An enhanced Th1 immune response may include an increase in one or more of the cytokines associated with a Th1 immune response (such as IFNγ), and an increase in activated macrophages.

An enhanced Th1 immune response may include one or more of an increase in antigen specific IgG antibodies, especially IgG1 antibodies.

For example, the immunogenic composition or the vaccine as described herein, may be in association (e.g. chemically or recombinantly linked, bound by affinity binding or a mixture of separate components) with one or more adjuvants and/or pharmaceutically acceptable excipients. The vaccine may include one or more pharmaceutically acceptable excipients or vehicles, such as water, saline, glycerol, ethanol, etc. Additionally, auxiliary substances, such as wetting or emulsifying agents, pH buffering substances, and the like, may be present in such vehicles. Adjuvants may specifically be used to enhance the effectiveness of the vaccine. Adjuvants may be added directly to the vaccine compositions or can be administered separately, either concurrently with or shortly after, administration of the vaccine.

Suitable adjuvants include cytokines and similar compounds which help orchestrate an immune response to the immunogen. As used herein, the term "cytokine" is used as a generic name for a diverse group of soluble proteins and peptides which act as humoral regulators at nano-to picomolar concentrations and which, either under normal or pathological conditions, modulate the functional activities of individual cells and tissues. These proteins also mediate interactions between cells directly and regulate processes taking place in the extracellular environment.

Examples of cytokines include IL-1, IL-4, TNFα, IFNα, INFγ, GM-CSF, G-CSF

CpG oligonucleotides can also be used as an adjuvant in conjunction with presentation of respective epitopes. Other adjuvants include alum, (in)complete Freund's adjuvant, *B. pertussis* or its toxin, IC31, etc.

The components of the immunogenic composition, which are: the directed adjuvant component, e.g. the anti-CD32 moiety linked to the TLR9 ligand and the first peptidic alpha-helix; and the immunogen component, e.g. comprising the peptide immunogen linked to the second peptidic alpha-helix that matches the first one, as well as the immunogenic composition or the vaccine, or any of its binding moieties or ligands and the immunogen with our without the coil repeats may be obtained by various methods known in the art, e.g. by purification or isolation from cell culture, recombinant technology or by chemical synthesis.

According to a specific embodiment, the immunogenic composition and/or the directed adjuvant component and/or the immunogen component thereof, is produced as a recombinant polypeptide, such as by recombinant DNA technology. As used herein, the term "recombinant" refers to a molecule or construct that does not naturally occur in a host cell. In some embodiments, recombinant nucleic acid molecules contain two or more naturally-occurring sequences that are linked together in a way that does not occur naturally. A recombinant protein refers to a protein that is encoded and/or expressed by a recombinant nucleic acid. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. Recombinant cells contain at least one recombinant polynucleotide or polypeptide. "Recombination", "recombining", and generating a "recombined" nucleic acid generally encompass the assembly of at least two nucleic acid fragments. In certain embodiments, recombinant proteins and recombinant nucleic acids remain functional, i.e., retain their activity or exhibit an enhanced activity in the host cell.

Thus, the invention further refers to the production of the immunogenic composition or the components thereof, and the recombinant means for such production, including a nucleic acid encoding the amino acid sequence, an expression cassette, a vector or plasmid comprising the nucleic acid encoding the amino acid sequence to be expressed, and a host cell comprising any such means. Suitable standard recombinant DNA techniques are known in the art and described inter alia in Sambrook et al., "Molecular Cloning: A Laboratory Manual" (1989), 2nd Edition (Cold Spring Harbor Laboratory press).

Herein the term "subject" is understood to comprise human or mammalian subjects, including livestock animals, companion animals, and laboratory animals, in particular human beings, which are either patients suffering from a specific disease condition or healthy subjects.

The invention further provides a kit of components for preparing the immunogenic composition of the invention, e.g. a pharmaceutical kit comprising one or more containers filled with the components. The kits can be used in the above-described methods. In a particular embodiment, the kit further comprises instructions for using the components of the immunogenic composition or the prepared immunogenic composition or vaccine of the invention.

According to a specific example, the vaccine according to the invention comprises a recombinant polypeptide of the structure SEQ ID 9 or 10, as depicted in FIG. 5. In this example alpha-helix repeats are used. The preferred minimal functional number of repeats for the coils used is 3 and the preferred maximum functional number is 5[22-24] but more repeats are feasible depending on the type of alpha helix. Limiting would be the number of repeats that start to induce homodimerization. Thus, homodimerization is specifically excluded.

Similar polypeptides may comprise a leader sequence, the amino acid sequence of a specific anti-CD32 moiety, which is e.g. a recombinant scFv, a linker, a tag for purification purposes and the sequence of the peptidic alpha-helix pepE. This construct with or without the TLR9 ligand is also called "warhead", which may then be used to construct a vaccine by combination with an immunogen linked to the counter alpha helix pepK.

According to another specific example, the anti-CD32 moiety is an anti-CD32a peptide with the sequence of SEQ ID 37: ADGAWAWVWLTETAVGAAK[24] used as an alternative to the ScFv.

According to a further example, a stable coiled coil is established between the warhead scFv and the immunogen.

It has proven that PBMC could be effectively stimulated with such immunogen or vaccine.

In a further example it could be shown that the warhead mediated enhanced antigen presentation. T cells were effectively stimulated when the immunogen with the coil (the pepK coil) interacted with the warhead containing the counterpart coil (the pepE coil).

In further examples treatment of non-human primates is described, using the vaccine of the invention, triggering effective B-cell response and T-cell response, in particular cytotoxic T-cell response. Such B-cell response and T-cell response is particularly reversible, thus, avoiding undesired autoimmune reactions.

In a specific example, it has proven that antisera induced antibody response and ADCC activity.

Therefore, the present invention provides for a unique immunogenic composition and vaccine, and respective applications.

The foregoing description will be more fully understood with reference to the following examples. Such examples are, however, merely representative of methods of practicing one or more embodiments of the present invention and should not be read as limiting the scope of invention.

EXAMPLES

In the following, the examples refer to the specific use of exemplary immunogenic compositions termed OQR200. If not indicated otherwise, the OQR200 as used herein comprises the Her2/neu domain of Cynomolgus monkeys origin (also termed OQR200m), specifically for use in the in vivo monkey studies. It is understood that human OQR200 (also termed OQR200h) is likewise produced and used, e.g. in the monkey model or in particular for human use.

Example 1: Materials

Example 1a: Amino Acid-Sequence CyErb2-Coil (SEQ ID 9; Her2/Neu from Cynomolgus Monkeys Including pepK of the S-TIR Technology)

```
1          10         20         30         40
TQVCTGTDMK LRLPASPETH LDMLRHLYQG CQVVQGNLEL
```

-continued
```
50         51   60         70                  80
TYLPTNASLS FLQDIQEVQG YVLIAHNQVR QVPLQRLRIV 90              100  101        110                120
RGTQLFEDNY ALAVLDNGNP LNNTTPVTGA SPGGLRELQL 130             140         150  151           160
RSLTEILKGG VLIQRNPQLC YQDTILWKDI FHKNNQLALT 170             180         190                 200
LIDTNRSRAC HPCSPVCKGS RCWGESSEDC QSLTRIVCAG 201   210           220                230        240
GCARCKGPLP TDCCHEQCAA GCTGPKHSDC LACLHFNHSG 250  251       260                270                280
ICELHCPALV TYNTDTFESM PNPEGRYTFG ASCVTACPYN 290             300  301       310                320
YLSTDVGSCT LVCPLHNQEV TAEDGTQRCE KCSKPCARVC 330             340                350  351       360
YGLGMEHLRE VRAVTSANIQ EFAGCKKIFG SLAFLPESFD 370             380                390                 400
GDPASNTAPL QPEQLRVFET LEEITGYLYI SAWPDSLPDL 401   410           420                430                440
SVLQNLQVIR GRILHNGAYS LTLQGLGISW LGLRSLRELG 450  451       460                470                480
SGLALIHHNT RLCFVHTVPW DQLFRNPHQA LLHTANRPED 490             500  501       510                520
ECVGEGLACH QLCARGHCWG PGPTQCVNCS QFLRGQECVE 530             540                550  551       560
ECRVLQGLPR EYVNARHCLP CHPECQPQNG SVTCFGPEAD 570             580                590                 600
QCVACAHYKD PPFCVARCPS GVKPDLSYMP IWKFPDEEGT 601   610           620                630                640
CQSCPINCTH SCVDLDDKGC PAEQRASPLT GSGHHHHHG 650  651       660                670                680
GGSGGKVSAL KEKVSALKEK VSALKEKVSA LKEKVSALKE
```

The linker between Her2 and pepK (italics) containing the HIS tag is underlined (SEQ ID 4: GGGSHHHHHHGGGSGG) and may be replaced by any other linker e.g. GGGSGGGS (SEQ ID 5)

Example 1b: Amino Acid-Sequence Erb2-Coil (SEQ ID 10; Her2/Neu from Humans Including pepK of the S-TIR Technology)

```
1          10         20         30         40
TQVCTGTDMK LRLPASPETH LDMLRHLYQG CQVVQGNLEL 50         51   60         70                  80
TYLPTNASLS FLQDIQEVQG YVLIAHNQVR QVPLQRLRIV 90              100  101        110                120
RGTQLFEDNY ALAVLDNGNP LNNTTPVTGA SPGGLRELQL 130             140         150  151           160
RSLTEILKGG VLIQRNPQLC YQDTILWKDI FHKNNQLALT 170             180         190                 200
LIDTNRSRAC HPCSPVCKGS RCWGESSEDC QSLTRIVCAG 201   210           220                230        240
GCARCKGPLP TDCCHEQCAA GCTGPKHSDC LACLHFNHSG 250  251       260                270                280
ICELHCPALV TYNTDTFESM PNPEGRYTFG ASCVTACPYN
```

```
            290         300 301     310         320
YLSTDVGSCT  LVCPLHNQEV  TAEDGTQRCE  KCSKPCARVC 330         340         350 351     360
YGLGMEHLRE  VRAVTSANIQ  EFAGCKKIFG  SLAFLPESFD 370         380         390         400
GDPASNTAPL  QPEQLRVFET  LEEITGYLYI  SAWPDSLPDL 401         410         420         430         440
SVLQNLQVIR  GRILHNGAYS  LTLQGLGISW  LGLRSLRELG 450 451     460         470         480
SGLALIHHNT  RLCFVHTVPW  DQLFRNPHQA  LLHTANRPED 490         500 501     510         520
ECVGEGLACH  QLCARGHCWG  PGPTQCVNCS  QFLRGQECVE 530         540         550 551     560
ECRVLQGLPR  EYVNARHCLP  CHPECQPQNG  SVTCFGPEAD 570         580         590         600
QCVACAHYKD  PPFCVARCPS  GVKPDLSYMP  IWKFPDEEGT 601         610         620         630         640
CQSCPINCTH  SCVDLDDKGC  PAEQRASPLT  GSGHHHHHHG 650 651     660         670         680
GGSGGKVSAL  KEKVSALKEK  VSALKEKVSA  LKEKVSALKE
```

The linker between Her2 and pepK (italics) containing the HIS tag is underlined (SEQ ID 4: GGGSHHHHHHGGGSGG) and may be replaced by any other linker e.g. GGGSGGGS (SEQ ID 5).

Example 1c: Amino Acid-Sequence Erb2-Coil
(SEQ ID 38; Her2/Neu from Humans Including pepK of the S-TIR Technology)

```
1           10          20          30          40
TQVCTGTDMK  LRLPASPETH  LDMLRHLYQG  CQVVQGNLEL 50          51          60          70          80
TYLPTNASLS  FLQDIQEVQG  YVLIAHNQVR  QVPLQRLRIV 90          100 101     110         120
RGTQLFEDNY  ALAVLDNGNP  LNNTTPVTGA  SPGGLRELQL 130         140         150 151     160
RSLTEILKGG  VLIQRNPQLC  YQDTILWKDI  FHKNNQLALT 170         180         190         200
LIDTNRSRAC  HPCSPVCKGS  RCWGESSEDC  QSLTRIVCAG 201         210         220         230         240
GCARCKGPLP  TDCCHEQCAA  GCTGPKHSDC  LACLHFNHSG 250 251     260         270         280
ICELHCPALV  TYNTDTFESM  PNPEGRYTFG  ASCVTACPYN 290         300 301     310         320
YLSTDVGSCT  LVCPLHNQEV  TAEDGTQRCE  KCSKPCARVC 330         340         350 351     360
YGLGMEHLRE  VRAVTSANIQ  EFAGCKKIFG  SLAFLPESFD 370         380         390         400
GDPASNTAPL  QPEQLRVFET  LEEITGYLYI  SAWPDSLPDL 401         410         420         430         440
SVLQNLQVIR  GRILHNGAYS  LTLQGLGISW  LGLRSLRELG 450 451     460         470         480
SGLALIHHNT  RLCFVHTVPW  DQLFRNPHQA  LLHTANRPED 490         500 501     510         520
ECVGEGLACH  QLCARGHCWG  PGPTQCVNCS  QFLRGQECVE 530         540         550 551     560
ECRVLQGLPR  EYVNARHCLP  CHPECQPQNG  SVTCFGPEAD 570         580         590         600
QCVACAHYKD  PPFCVARCPS  GVKPDLSYMP  IWKFPDEEGT 601         620         630         640         650
CQSCPINCTH  SCVDLDDKGC  PAEQRASPLT  SSGGGSGGKV 660 661     670         780
SALKEKVSAL  KEKVSALKEK  VSALKEKVSA  LKE
```

The linker between Her2 and pepK (italics) does not contain the HIS tag and is underlined (SEQ ID 39: SSGGGSGG) and may be replaced by any other linker consisting of G and S amino acid residues of e.g. 5-30 amino acid length, such as GGGSGGGS (SEQ ID 5).

Example 1d: ScFV Warhead Containing Coil:
Amino Acid Sequence of ScFV-Coil1 (SEQ ID 3)

```
1           10          20          30          40
MELGLSWIFL  LAILKGVQCE  VQLQQSGPEL  KKPGETVKIS 50 51       60          70          80
CKASGYTFTN  YNWVKQAPGK  GLKWMGWLNT  YTGESIYPDD 90          100 101     110         120
FKGRFAFSSE  TSASTAYLQI  NNLKGMNEDM  ATYFCARGDY 130         140         150 151     160
GYDDPLDYWG  QGTSVIVSSG  GGGSGGGGSG  SGGGDIVMTQ 170         180         190         200
AAPSVPVTPG  ESVSISCRSS  KSLLHTNGNT  YLHWFLQRPG 201         210         220         230         240
QSPQLLIYRM  SVLASGVPDR  FSGSGSGTAF  TLSISRVEAE 250 251     260         270         280
DVGVFYCMQH  LEYPLTFGAG  TKLELKGSIS  AWSHPQFEKG 290         300 301     310
PEVSALEKEV  SALEKEVSAL  EKEVSALEKE  VSALEK
```

AA 1-19: leader sequence (to secrete the product)

IAA 20-271 sequence of ScFV (the VH domain is underlined, VI is double underlined) order of VH and VL domain may be swapped)

IAA140-154 Linker may be changed to any linker used in ScFV preparation

AA 272-279: StrepTag II for purification may be exchanged to any type of tag e.g. flag tag or HIS tag.

AA280-281: short linker (may be longer)

AA282-316: heptad repeat alpha helix (pepE) to form the coiled coil with the counter heptad repeat alpha helix in the immunogen (pepK). In the example 5 repeats are used, more repeats may cause auto-aggregation and less repeats will reduce the affinity, however 4 repeats are still functional. The minimal functional number of repeats for the coils used is 3 and 5

A TRL9 agonist such as CpG may be coupled to the warhead using a chemical coupling e.g. using the Solulink antibody-oligo coupling KIT. A peptidic TRL9 agonist may be coupled using standard peptide chemistry. There are three classes of CpG, all may be used to prepare a warhead from a ScFV-coil1:

```
CPG class A
Group CpG-A:
e.g. ODN2216:
                                        (SEQ ID 6)
GGGGGACGATCGTCGGGGGG CpG class B
Group CpG-B:
e.g. ODN2006:
                                        (SEQ ID 7)
TCGTCGTTTTGTCGTTTTGTCGTT CPG class C
Group CpG-C
e.g. ODNM362:
                                        (SEQ ID 8)
TCGTCGTCGTTCGAACGACGTTGAT
```

Example 2: Method for Expression, Production and Purification of CyHerb2-Coil

Cloning of Gene CyErbB2-His6-pepK on pTT5:

The DNA coding the extracellular domain of the Cynomolgus epidermal growth factor receptor 2 (CyErbB2: accession number: EHH58073.1) fused to a His6 tag and pepK (see example 1a) was synthesized by GeneART (construct ID: 14AFGWKC).

The final expression vector was obtained by cloning the synthesized gene in the pTT5 vector by digestion with EcoRI/BamHI (NEB#R0101/NEB#R0136, respectively) and standard molecular biology procedures. Shortly, 3.5 µg of pTT5 vector and 1 µg of GeneArt plasmid DNA (containing the gene) were digested with 20 U or 10 U of each enzyme in NEB3.1 buffer, respectively. The vector (approx. 4.4 kb) and fragment (approx. 2.0 kb) were separated by agarose gel and purified using Illustra Gfx PCR DNA and gel band purification kit (GE#28-9034-71) following kit instructions. Thereafter, vector (50 ng) and fragment (60 ng) were ligated using 200 U of T4 DNA ligase and the corresponding buffer (NEB#M020L). After an overnight incubation at 16° C., 5 µL of the ligation was transformed into 20 µL of NEB10beta chemically competent cells (NEB#C3019H). Six colony forming units (cfu) were used for inoculation of larger cultures and plasmid isolation using Qiaprep Spin Miniprep kit (Qiagen#27106). The correct cloning of the DNA containing the immunogen was first confirmed by digestion of plasmids with BamHI and NheI-HF (NEB#R0131) and then re-confirmed by DNA sequencing. Larger quantities of the DNA were prepared following manufactures' instructions of Qiagen Endofree plasmid Maxi kit#12381 or NucleoBond® Xtra Midi#740410.50.

Transfection of HEK293-6E with Polyethylenimine:

The expression vector harboring CyErbB2-His6-pepK gene was transfected in HEK293-6E suspension cells using linear Polyethylenimine (PEI). PEIpro™ (Polyplus#115-010) was mixed into the DNA solution in a ratio 1:2 (volume: mass). Commonly, 1 mg of DNA is used for transfecting 1 L of HEK293-6E cells at a density between 1.5-2×10^6/mL in medium Freestyle F17 (Invitrogen#A13835-01) supplemented with 4 mM L-Glutamine (PAA#M11-004; 200 mM), Geneticin G418 50 µg/mL (Gibco#10131-027; 50 mg/mL) and Pluronic F-68 (Gibco#24040-032; 10%). After mixing, the complex PEI:DNA was added dropwise to 1 L flasks containing each 330 ml cell suspension in Freestyle-F17 media.

Purification of CyErbB2-His6-pepK Protein:

Five days post transfection, the cultures were harvested and cells pelleted by centrifugation at 6000 rpm for 30 min. The supernatant was further filtered through a Sartopore 2 150 membrane (sartorius#5441307H4-SS) with a cut off of 0.45+0.2 µm. Phenylmethanesulfonyl fluoride solution (PMSF, SIGMA#93482) was added to the filtrate to a final concentration of 0.1 mM to inhibit protease activity. Media was dialyzed against 1× phosphate buffer saline (PBS) (PBS 10×, Gibco#70013 or Lonza#BE17-5179) using a tangential flow filtration (TFF) device Millipore Labscale TFF system connected to three 10 kDa cut off TFF-cassettes (Merck-Millipore#PXC010C50). The filtrate was concentrated 50 times before the media was exchanged using at least 7 volumes of the buffer. The final concentrate was supplemented with imidazole 0-40 mM ((Merck#1.04716.0250) and a protease inhibitor cocktail (Complete, EDTA-free, Roche#05056489001). Upon removing particles by filtration over 0.45 µm pore size, the CyErbB2-His6-pepK (immunogen) was purified from the concentrate through the His tag. For that purpose, a HisTRAP HP column (GE#29-0510-21) was installed in a Äkta purifier system (GE). Sample was loaded at a flow rate of 0.5 ml/min which was not altered thereafter. Upon completion, PBS containing 30 mM imidazole was added without changing the flow rate till absorbance signal was dropping to a plateau. After a washing step with PBS-75 mM imidazole, the immunogen was eluted with PBS-300 mM imidazole. Fractions of 1 mL were collected and the ones containing the eluted peak were finally pooled and dialyzed in order to remove the imidazole.

Example 3: Method for Production of OQR200

For the production of OQR200, Warhead (Example 1d) and CyErb2-coil (Example 1a) were mixed in molar ratio of 1:1 and incubated for 1 h on ice. Subsequently the solution was sterilized using an 0.22 µm milipore filter and finally adsorbed to Alum under constant rotation for 12 h at 4° C. OQR200 was stored at 4° C. until use.

For the production of OQR200 for use in human subjects, the human Her2/neu antigen has been used. Warhead (Example 1d) and Erb2-coil (Her2/neu from humans including pepK of the S-TIR technology, Example 1c) were mixed in molar ratio of 1:1 and incubated for 1 h on ice. Subsequently the solution was sterilized using a 0.22 µm milipore filter and finally adsorbed to Alum under constant rotation for 12 h at 4° C. OQR200 (human Her2/neu) was stored at 4° C. until use.

Example 4: In Vivo Induction of Anti-Autologous Her2 Immune Responses

Example 4a: OQR200h

Cynomolgus monkeys are immunized s.c. with 500 µl containing 167 µg OQR200h (formulated on Alum, produced as described in Example 3, however employing Erb2-coil (Example 1b) instead of the CyErb2-coil (Example 1a)) on d1, d15, d35 and boosted on d56 or d127. Blood samples for serum preparation are taken weekly always before immunization starting at d-7. Serum is stored at −200 C until use. PBMC are purified for T cell experiments of d1 and d79 (2 weeks after boost) and immediately tested for antigen specific proliferation.

Example 4b: OQR200m (Herein Also Referred to as OQR200)

Cynomolgus monkeys were immunized s.c. with 500 µl containing 167 µg OQR200 (formulated on Alum, produced as described in Example 3), on d1, d15, d35 and boosted on d56 or d127. Blood samples for serum preparation were taken weekly always before immunization starting at d-7. Serum was stored at −200 C until use. PBMC are purified for T cell experiments of d1 and d79 (2 weeks after boost) and immediately tested for antigen specific proliferation.

Example 5: Detection of Antibody Response after Application of OQR200

Method:

96 well plates (Maxisorp Thermo 442404) were coated with 1 µg/ml Her2-His less in PBS (10× diluted PBS Lonza 10×: BE17-517Q) at 4° C., overnight. The plates were washed twice with PBST (PBS+0.05% Tween 20, SIGMA P1379-500ML), followed by blocking for one hour with 3% BSA (fraction V Sigma A4919-25g) in PBST The whole assay was done at room temperature. After 3 times washing with PBST, the plates were incubated for 1 hour with 1% monkey serum in PBS. The plates were washed tree times and anti hIgG-AP 1:5000 (AbDSerotec 5211-8104) was incubated for 1 hour. After washing 3 times Streptavidin-HRP (GE RPN1231V) 1:5000 in PBST was added for 1 hour. The plates were washed 3 times and TMB (SIGMA T0440-1L) was added. After 15 min incubation, the reaction was stopped with H2SO4 30%, (Merck 1.00716.1000). The plates were read at 450-620 nm at Tecan infinite M2.

Results:

After immunization with OQR200m on d1, d15 and d36 (FIG. 1, stars) IgG anti Her2 antibodies could be detected. Representative examples of 3 animals are shown in FIG. 1 (closed triangles). First antibodies against Her2 were detected before $2^{nd}$ immunization on d15. Peak antibody titers were seen 2 weeks after $2^{nd}$ and $3^{rd}$ immunization after which titers started to decline until the next boost (d36 and d127), which induced a new strong increase in antibody titer. These results indicate reversibility of the treatment and the absence of treatment induced autoimmune disease.

Example 6: Biological Activity of Induced Antibody Response: ADCC

Method:

5000 SKBR3 cells (CLS 300333) were seeded per well in a 96 well plate. Medium used for culturing was DMEM (Gibco 10938-025) with Pen Strep Glutamine 1:100 (Gibco 10378-016) and 10% FCS (Sigma F2442) and incubated for 22-24 h, 37° C., 5% CO2. Monkey sera were inactivated for 30 min on 56° C. After incubation an ADCC kit (Promega G7010) was used.

In short: medium was replaced by 25 µl medium of the kit. 25 µl 10% heat inactivated monkey serum was added, followed by 25 µl effector cells. The wells were incubated for 6 hours at 37° C. and 5% CO2. After 15 minutes at room temperature, 75 µl Bio GLO Luciferase Assay reagent was added. After 20 min. the supernatant was transferred to 96 well white plate (Costar 3912). Luciferase activity as a measure for cell killing was measured with a Tecan infinite M2. Killing is shown relative to d1

Results:

Monkey sera from d28, d35, d42, d49, d63 and d70 were tested for the capacity to kill Her2 expressing SKBR3 cells. Sera were 1/100 diluted. Maximum killing was seen 2 weeks after $3^{rd}$ immunization (FIG. 2), at the top of the IgG time curve (see FIG. 1). Killing at d63 was stronger than at d56 despite that total IgG against Her2 was lower at that day (see FIG. 1) indicating that the quality of the anti Her2 antibodies has improved due to affinity maturation.

Example 7: Biological Activity of Induced Antibody Response: Competition with Trastuzumab (Herceptin) and Pertuzumab (Perjeta)

Method:

96 well plates (Maxisorp Thermo 442404) were coated with 0.5 µg/ml Her2-His less in PBS (10× diluted PBS Lonza 10×: BE17-517Q) at 4° C., overnight. The plates were washed twice with PBST (PBST+0.05% Tween 20, SIGMA P1379-500ML), followed by blocking for one hour with 3% BSA (fraction V Sigma A4919-25g) in PBST. After 3 times washing with PBST, the plates were incubated for 30 minutes on ice with 20% monkey serum. 100 ng/ml Pertuzumab-biotin or Trastuzumab-biotin was added for 30 min. on ice. The plates were washed tree times and Streptavidin-HRP (GE RPN1231V) 1:5000 in PBST was added. After 1 hour incubation at Room temperature the plates were washed 3 times and TMB (SIGMA T0440-1L) was added. After 15 min incubation the reaction was stopped with H2S04 30%, (Merck 1.00716.1000).

The plates were read at 450-620 nm at Tecan infinite M2. % inhibition was calculated by the following formula:

$$1 - \frac{(O.D \text{ value of the biotinylated detection antibody in the absence of monkey serum})}{O.D \text{ value of the biotinylated detection antibody in the presence of 20\% serum}} * 100\%$$

Results:

Animals were immunized with OQR200 on d1, d15, and d35. Sera taken between d50 and d88 were tested for their ability to block binding of Trastuzumab (FIG. 3, closed triangles, left Y-axis) and Pertuzumab (FIG. 3, open triangles, left Y-axis) to human Her2 in ELISA. Despite decreasing anti Her2 IgG titers between d50 and d88 (FIG. 3, blocks, right Y-axis) both Trastuzumab and Pertuzumab were more efficiently prevented from binding to their respective epitopes with sera taken at later time points after immunization. Optimal blocking was seen between d77 and d85. These results show that the quality of the anti Her2 antiserum increases over time by means of affinity maturation.

Example 8: Biological Activity of Induced Antibody Response: Proliferation Inhibition of Her2/Neu Expressing Tumor Cells Method:

5000 SKBR3 cells (CLS 300333) were seeded per well in a 96 well plate (Costar 3603). Culture medium (DMEM-CM) used for culturing was DMEM (Gibco 10938-025) with Pen Strep Glutamine 1:100 (Gibco 10378-016) and 10% FCS (Sigma F2442). The cells were incubated for 22-24 h, 37° C., 5% CO2.

Monkey sera were inactivated for 30 min on 56° C. and diluted to a final concentration of 10% with DMEM-CM. The medium of the plates was replaced by the monkey sera samples and after 72 hours incubation at 37° C., 5% CO2 10% Alamar Blue (Invitrogen DAL1025) was added to the wells. After 3 hours fluorescence which corresponds to cell metabolic activity was measured at 560-590 nm. As positive control Trastuzumab (at optimal concentration of 10 µg/ml)

and Pertuzumab (at optimal concentration of 10 µg/ml) were spiked in DMEM-CM containing 10% normal monkey serum.

Results:

Animals were immunized with OQR200 on d1, d15, and d35. Sera taken at day 64 were tested for their ability to inhibit proliferation of a Her/neu expressing breast cancer cell line (SKBR3) (FIG. 4, closed, hatched and open bar with thin borders; G1.1, G1.2, G1.3) and compared to clinically effective block buster antibodies Trastuzumab (Herceptin; crossed bar and thick border)) and Pertuzumab (Perjeta; hatched bar thick border). Monkey sera were comparable to Herceptin and better than Perjeta in inhibiting SKBR3 proliferation Example 9: Induction of T Cell Responses Against Autologous Her2

Method:

PBMCs (100.000/well) of OQR200 treated Cynomolgus monkeys were incubated for 3 days with 30 µg/ml CyErb2 (Her2/neu from cynomolgus monkeys) at 37° C./5% CO2. As a positive control PBMCs were incubated with 30 µg/ml ScFV (protein backbone of warhead present in OQR200).

Proliferation was assayed by the incorporation of [3|H]-thymidine (0.5 Ci/well) during the final 18 hrs of a 2-day culture. Cells were harvested for β-scintillation counting (Topcount NXT, Packard, Ramsey, Minn., USA). T cells before immunization did not respond to either antigen but after immunization T cells responded to both, the ScFV and CyErb2, as indicated by an increase [3|H]-thymidine uptake after immunization.

REFERENCE LIST

1. Mathis, D. and C. Benoist. 2004. Back to central tolerance. *Immunity* 20:509-516.
2. Miller, J. F. A. P. and G. Morahan. 1992. Peripheral T cell tolerance. *Annu. Rev. Immunol.* 10:51-69.
3. Tafuri, A., J. Alferink, P. Möller, G. J. Hämmerling, and B. Arnold. 1995. T cell awareness of paternal alloantigens during pregnancy. *Science* 270:630-633.
4. Cheever, M. A. and C. S. Higano. 2011. PROVENGE (Sipuleucel-T) in prostate cancer: the first FDA-approved therapeutic cancer vaccine. *Clin. Cancer Res.* 17:3520-3526.
5. Linley, A. J., M. Ahmad, and R. C. Rees. 2011. Tumour-associated antigens: considerations for their use in tumour immunotherapy. *Int. J. Hematol.* 93:263-273.
6. Eaton-Bassiri, A., S. B. Dillon, M. Cunningham, M. A. Rycyzyn, J. Mills, R. T. Sarisky, and M. L. Mbow. 2004. Toll-like receptor 9 can be expressed at the cell surface of distinct populations of tonsils and human peripheral blood mononuclear cells. *Infect. Immun.* 72:7202-7211.
7. Saikh, K. U., T. L. Kissner, A. Sultana, G. Ruthel, and R. G. Ulrich. 2004. Human monocytes infected with *Yersinia pestis* express cell surface TLR9 and differentiate into dendritic cells. *J. Immunol.* 173:7426-7434.
8. Tanaka, J., K. Sugimoto, K. Shiraki, M. Tameda, S. Kusagawa, K. Nojiri, T. Beppu, K. Yoneda, N. Yamamoto, K. Uchida, T. Kojima, and Y. Takei. 2010. Functional cell surface expression of toll-like receptor 9 promotes cell proliferation and survival in human hepatocellular carcinomas. *Int. J Oncol.* 37:805-814.
9. Hartmann, G., J. Battiany, H. Poeck, M. Wagner, M. Kerkmann, N. Lubenow, S. Rothenfusser, and S. Endres. 2003. Rational design of new CpG oligonucleotides that combine B cell activation with high IFN-a induction in plasmacytoid dendritic cells. *Eur. J. Immunol.* 33:1633-1641.
10. Tversky, J. R., A. P. Bieneman, K. L. Chichester, R. G. Hamilton, and J. T. Schroeder. 2010. Subcutaneous allergen immunotherapy restores human dendritic cell innate immune function. *Clin. Exp. Allergy.* 40:94-102.
11. Abel, K., Y. Wang, L. Fritts, E. Sanchez, E. Chung, P. Fitzgerald-Bocarsly, A. M. Krieg, and C. J. Miller. 2005. Deoxycytidyl-deoxyguanosine oligonucleotide classes A, B, and C induce distinct cytokine gene expression patterns in rhesus monkey peripheral blood mononuclear cells and distinct alpha interferon responses in TLR9-expressing rhesus monkey plasmacytoid dendritic cells. *Clin Diagn. Lab Immunol* 12:606-621.
12. Puig, M., K. W. Tosh, L. M. Schramm, L. T. Grajkowska, K. D. Kirschman, C. Tami, J. Beren, R. L. Rabin, and D. Verthelyi. 2012. TLR9 and TLR7 agonists mediate distinct type I IFN responses in humans and nonhuman primates in vitro and in vivo. *J Leukoc. Biol.* 91:147-158.
13. Arndt, K. M., K. M. Muller, and A. Pluckthun. 2001. Helix-stabilized Fv (hsFv) antibody fragments: substituting the constant domains of a Fab fragment for a heterodimeric coiled-coil domain. *J Mol. Biol.* 312:221-228.
14. Van Reijsen, F. C., C. A. F. M. Bruijnzeel-Koomen, F. S. Kalthoff, E. Maggi, S. Romagnani, J. K. T. Westland, and G. C. Mudde. 1992. Skin-derived aeroallergen-specific T-cell clones of Th2 phenotype in patients with atopic dermatitis. *J. Allergy Clin. Immunol.* 90:184-193.
15. Krieg, A. M., A. K. Yi, S. Matson, T. J. Waldschmidt, G. A. Bishop, R. Teasdale, G. A. Koretzky, and D. M. Klinman. 1995. CpG motifs in bacterial DNA trigger direct B-cell activation. *Nature.* 374:546-549.
16. Chao, H., D. L. Bautista, J. Litowski, R. T. Irvin, and R. S. Hodges. 1998. Use of a heterodimeric coiled-coil system for biosensor application and affinity purification. *J. Chromatogr. B Biomed. Sci. Appl.* 715:307-329.
17. Litowski, J. R. and R. S. Hodges. 2001. Designing heterodimeric two-stranded alpha-helical coiled-coils: the effect of chain length on protein folding, stability and specificity. *J. Pept. Res.* 58:477-492.
18. Litowski, J. R. and R. S. Hodges. 2002. Designing heterodimeric two-stranded alpha-helical coiled-coils. Effects of hydrophobicity and alpha-helical propensity on protein folding, stability, and specificity. *J. Biol. Chem.* 277:37272-37279.
19. Greenman, J., A. L. Tutt, A. J. George, K. A. Pulford, G. T. Stevenson, and M. J. Glennie. 1991. Characterization of a new monoclonal anti-Fc gamma RII antibody, AT10, and its incorporation into a bispecific F(ab')2 derivative for recruitment of cytotoxic effectors. *Mol. Immunol* 28:1243-1254.
20. Stuart, S. G., M. L. Trounstine, D. J. Vaux, T. Koch, C. L. Martens, I. Mellman, and K. W. Moore. 1987. Isolation and expression of cDNA clones encoding a human receptor for IgG (Fc gamma RII). *J. Exp. Med.* 166:1668-1684.
21. Macintyre, E. A., P. J. Roberts, R. bdul-Gaffar, K. O'Flynn, G. R. Pilkington, F. Farace, J. Morgan, and D. C. Linch. 1988. Mechanism of human monocyte activation via the 40-kDa Fc receptor for IgG. *J Immunol.* 141:4333-4343.
22. Krug, A., S. Rothenfusser, V. Hornung, B. Jahrsdorfer, S. Blackwell, Z. K. Ballas, S. Endres, A. M. Krieg, and G. Hartmann. 2001. Identification of CpG oligonucleotide sequences with high induction of IFN-alpha/beta in plasmacytoid dendritic cells. *Eur J Immunol.* 31:2154-2163.

23. Tel, J., N. Beenhakker, G. Koopman, B. Hart, G. C. Mudde, and V. de, I. 2012. Targeted delivery of CpG ODN to CD32 on human and monkey plasmacytoid dendritic cells augments IFNalpha secretion. *Immunobiology.* 217: 1017-1024.
24. Berntzen, G., J. T. Andersen, K. Ustgard, T. E. Michaelsen, S. A. Mousavi, J. D. Qian, P. E. Kristiansen, V. Lauvrak, and I. Sandlie. 2009. Identification of a high affinity Fcgamma RIIA binding peptide that distinguishes Fcgamma RIIA from Fcgamma RIIB and exploits Fcgamma RIIA mediated phagocytosis and degradation. *J. Biol. Chem.* 284:1126-1135.
25. Milani, A., D. Sangiolo, F. Montemurro, M. Aglietta, and G. Valabrega. 2013. Active immunotherapy in HER2 overexpressing breast cancer:current status and future perspectives. *Annals of Oncology.* 24:1740-1748.

The invention claimed is:

1. An immunogenic composition comprising:
    (a) a directed adjuvant comprising an anti-CD32 binding moiety linked to a TLR9 ligand and a first peptidic alpha-helix, wherein the anti-CD32 binding moiety is an anti-CD32 antibody or an antigen-binding fragment thereof, and wherein the TLR9 ligand is a TLR9 agonist selected from the group consisting of a CpG oligodeoxynucleotide class A molecule, a CpG oligodeoxynucleotide class B molecule, and a CpG oligodeoxynucleotide class C molecule; and
    (b) at least one immunogen comprising an extracellular Her2/neu domain monomer that is linked to a second peptidic alpha-helix that is bound to the first alpha-helix to form a coiled coil, wherein the extracellular Her2/neu domain monomer comprises:
        (i) a polypeptide identified by the amino acid sequence SEQ ID NO:1 or SEQ ID NO:2; or
        (ii) a polypeptide with at least 90% sequence identity to the polypeptide of subparagraph (i);
    wherein the first and second peptidic alpha-helices each comprise 2-9 repeats of a matching amino acid sequence selected from the group consisting of SEQ ID NOs:11, 12, and 15-20.

2. The immunogenic composition of claim 1, comprising at least two immunogens linked to the second peptidic alpha-helix.

3. The immunogenic composition of claim 1, wherein each of said first and second alpha-helices specifically bind to each other with a Kd of less than $10^{-6}$ M.

4. The immunogenic composition of claim 1, comprising one or more linker sequences composed of glycine, serine, and/or lysine residues.

5. The immunogenic composition of claim 1, wherein the immunogen comprises the amino acid sequence of SEQ ID NO:9 or SEQ ID NO:10.

6. A vaccine comprising the immunogenic composition of claim 1 and a pharmaceutically acceptable carrier.

7. A kit for preparing the immunogenic composition of claim 1, comprising the following components:
  (a) a directed adjuvant comprising an anti-CD32 binding moiety linked to a TLR9 ligand and a first peptidic alpha-helix, wherein the anti-CD32 binding moiety is an anti-CD32 antibody or an antigen-binding fragment thereof, and wherein said TLR9 ligand is a TLR9 agonist selected from the group consisting of a CpG oligodeoxynucleotide class A molecule, a CpG oligodeoxynucleotide class B molecule, and a CpG oligodeoxynucleotide class C molecule; and
  (b) an immunogen comprising an extracellular Her2/neu domain monomer that is linked to a second peptidic alpha-helix coiled to the first alpha-helix, wherein the extracellular Her2/neu domain comprises or consists of:
    (i) a polypeptide identified by the amino acid sequence SEQ ID NO:1 or SEQ ID NO:2; or
    (ii) a polypeptide with at least 90% sequence identity to the polypeptide of subparagraph (i);
  wherein the first and second peptidic alpha-helices each comprise 2-9 coil repeats of a matching amino acid sequence selected from the group consisting of SEQ ID NOs:11, 12, and 15-20, and wherein the first peptidic alpha-helix is capable of binding to the second peptidic alpha-helix to form a coiled coil.

8. A method of treating a subject suffering from Her2/neu positive tumor diseases, comprising administering the immunogenic composition of claim 1 to the subject.

9. The method of claim 8, wherein the composition is administered to the subject in an effective amount employing a prime-boost strategy.

10. The method of claim 8, wherein the composition is administered to the subject in an effective amount ranging between 0.0001 and 2 mg per administration.

11. The method of claim 8, wherein the subject is further treated by chemotherapy, immunotherapy, inhibitor therapy and/or radiotherapy.

12. The method of claim 8, wherein a protective immune response is triggered in the subject with a serum IgG titer against Her2/neu of at least 1/100.

13. The immunogenic composition of claim 1, wherein said Her2/neu domain consists of a polypeptide identified by the amino acid sequence of SEQ ID NO:1 or SEQ ID NO:2.

14. The immunogenic composition of claim 2, comprising 3 or 4 immunogens linked to the second peptidic alpha-helix.

15. The immunogenic composition of claim 1, wherein said anti-CD32 binding moiety binds to CD32a.

16. The immunogenic composition of claim 4, wherein the linker sequences comprise the amino acid sequence of SEQ ID NO:4 or SEQ ID NO:5.

17. The method of claim 8, wherein the subject is suffering from a disease selected from the group consisting of breast cancer, ovarian cancer, stomach cancer, uterine cancer, colorectal cancer and non-small cell lung cancer.

* * * * *